United States Patent [19]
Baumgartner et al.

[11] Patent Number: 6,080,406
[45] Date of Patent: Jun. 27, 2000

[54] HEMATOPOIETIC CYTOKINE RECEPTOR

[75] Inventors: James W. Baumgartner; Donald C. Foster; Frank J. Grant; Cindy A. Sprecher, all of Seattle, Wash.

[73] Assignee: ZymoGenetics, Inc., Seattle, Wash.

[21] Appl. No.: 09/275,925

[22] Filed: Mar. 24, 1999

Related U.S. Application Data

[60] Continuation of application No. 09/073,594, May 6, 1998, Pat. No. 5,925,735, which is a division of application No. 08/653,740, May 23, 1996, Pat. No. 5,792,850.

[51] Int. Cl.$^7$ .................................................. A61K 39/395
[52] U.S. Cl. ..................................... 424/143.1; 424/139.1; 530/387.9; 530/388.22
[58] Field of Search ............................... 424/143.1, 139.1; 530/388.22, 387.9

*Primary Examiner*—Christina Y. Chan
*Assistant Examiner*—Patrick J. Nolan
*Attorney, Agent, or Firm*—Gary E. Parker

[57] ABSTRACT

Novel receptor polypeptides, polynucleotides encoding the polypeptides, and related compositions and methods are disclosed. The polypeptides comprise an extracellular ligand-binding domain of a cell-surface receptor that is expressed at high levels in lymphoid tissue, including B-cells and T-cels. The polypeptides may be used within methods for detecting ligands that stimulate the proliferation and/or development of lymphoid and myeloid cells in vitro and in vivo. Ligand-binding receptor polypeptides can also be used to block ligand activity in vitro and in vivo.

5 Claims, 1 Drawing Sheet

Figure
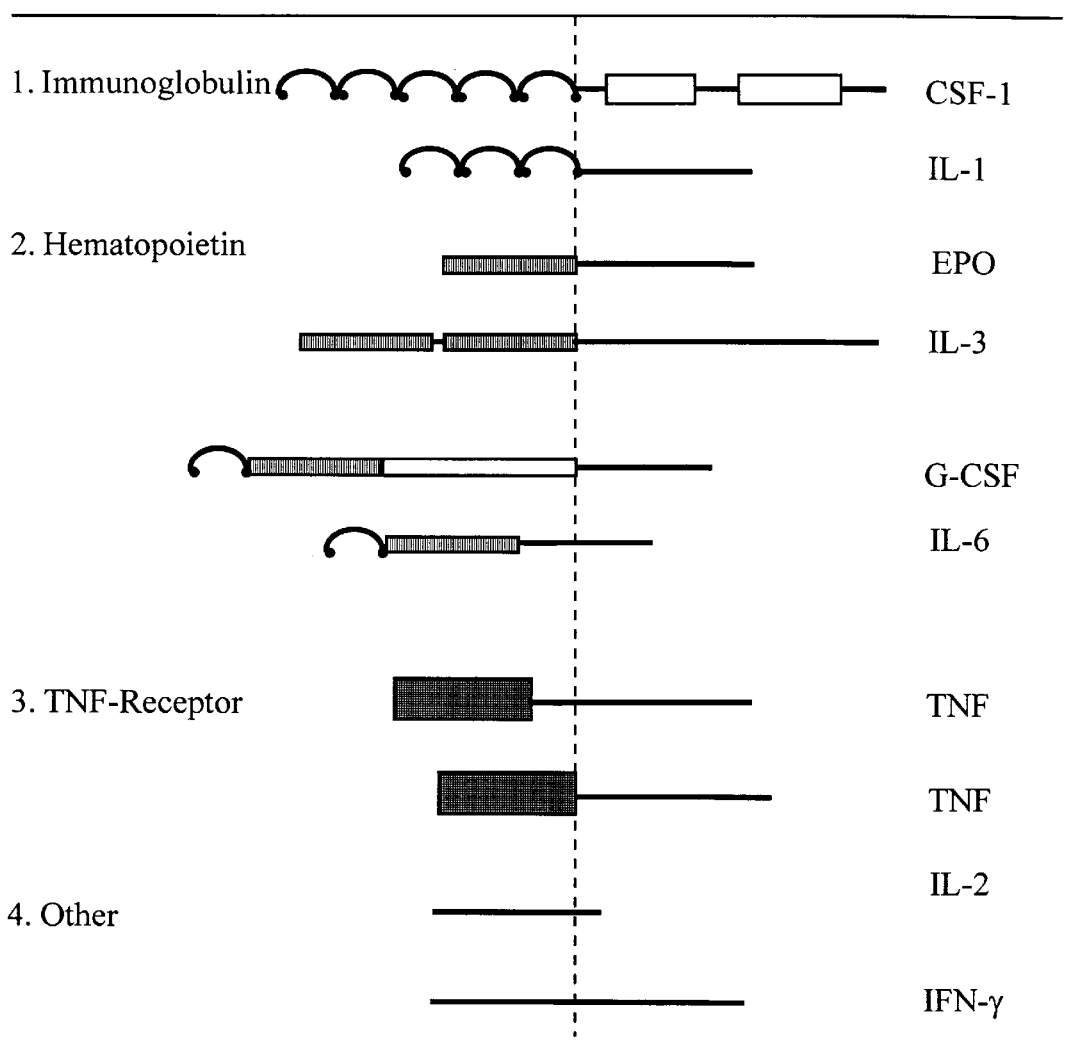
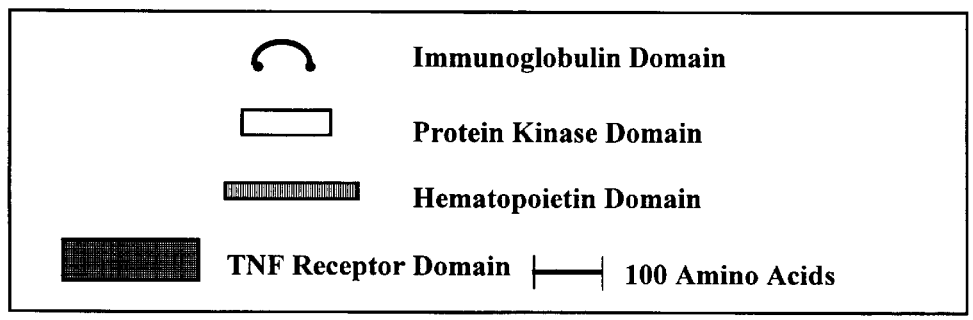

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /note= "Xaa is any amino acid."

(xi) SEQUENCE DESCRIPTION: SEQ ID NO:1:

Trp Ser Xaa Trp Ser
1               5

(2) INFORMATION FOR SEQ ID NO:2:

(i) SEQUENCE CHARACTERISTICS:
              (A) LENGTH: 2368 base pairs
              (B) TYPE: nucleic acid
              (C) STRANDEDNESS: double
              (D) TOPOLOGY: linear (ii) MOLECULE TYPE: cDNA (ix) FEATURE:
              (A) NAME/KEY: CDS
              (B) LOCATION: 23..1759

(xi) SEQUENCE DESCRIPTION: SEQ ID NO:2:

```
CTCGGGGCTC CCGAGGGACG CC ATG CGG GGA GGC AGG GGC GCC CCT TTC TGG      52
                         Met Arg Gly Gly Arg Gly Ala Pro Phe Trp
                          1               5                  10

CTG TGG CCG CTG CCC AAG CTG GCG CTG CTG CCT CTG TTG TGG GTG CTT      100
Leu Trp Pro Leu Pro Lys Leu Ala Leu Leu Pro Leu Leu Trp Val Leu
             15                  20                  25

TTC CAG CGG ACG CGT CCC CAG GGC AGC GCC GGG CCA CTG CAG TGC TAC      148
Phe Gln Arg Thr Arg Pro Gln Gly Ser Ala Gly Pro Leu Gln Cys Tyr
                 30                  35                  40

GGA GTT GGA CCC TTG GGC GAC TTG AAC TGC TCG TGG GAG CCT CTT GGG      196
Gly Val Gly Pro Leu Gly Asp Leu Asn Cys Ser Trp Glu Pro Leu Gly
             45                  50                  55

GAC CTG GGA GCC CCC TCC GAG TTA CAC CTC CAG AGC CAA AAG TAC CGT      244
Asp Leu Gly Ala Pro Ser Glu Leu His Leu Gln Ser Gln Lys Tyr Arg
         60                  65                  70

TCC AAC AAA ACC CAG ACT GTG GCA GTG GCA GCC GGA CGG AGC TGG GTG      292
Ser Asn Lys Thr Gln Thr Val Ala Val Ala Ala Gly Arg Ser Trp Val
 75                  80                  85                  90

GCC ATT CCT CGG GAA CAG CTC ACC ATG TCT GAC AAA CTC CTT GTC TGG      340
Ala Ile Pro Arg Glu Gln Leu Thr Met Ser Asp Lys Leu Leu Val Trp
                 95                 100                 105

GGC ACT AAG GCA GGC CAG CCT CTC TGG CCC CCC GTC TTC GTG AAC CTA      388
Gly Thr Lys Ala Gly Gln Pro Leu Trp Pro Pro Val Phe Val Asn Leu
            110                 115                 120

GAA ACC CAA ATG AAG CCA AAC GCC CCC CGG CTG GGC CCT GAC GTG GAC      436
Glu Thr Gln Met Lys Pro Asn Ala Pro Arg Leu Gly Pro Asp Val Asp
        125                 130                 135

TTT TCC GAG GAT GAC CCC CTG GAG GCC ACT GTC CAT TGG GCC CCA CCT      484
Phe Ser Glu Asp Asp Pro Leu Glu Ala Thr Val His Trp Ala Pro Pro
    140                 145                 150

ACA TGG CCA TCT CAT AAA GTT CTG ATC TGC CAG TTC CAC TAC CGA AGA      532
Thr Trp Pro Ser His Lys Val Leu Ile Cys Gln Phe His Tyr Arg Arg
155                 160                 165                 170

TGT CAG GAG GCG GCC TGG ACC CTG CTG GAA CCG GAG CTG AAG ACC ATA      580
Cys Gln Glu Ala Ala Trp Thr Leu Leu Glu Pro Glu Leu Lys Thr Ile
                175                 180                 185

CCC CTG ACC CCT GTT GAG ATC CAA GAT TTG GAG CTA GCC ACT GGC TAC      628
Pro Leu Thr Pro Val Glu Ile Gln Asp Leu Glu Leu Ala Thr Gly Tyr
            190                 195                 200
```

-continued

| | | | | | | | | | | | | | | | |
|---|---|---|---|---|---|---|---|---|---|---|---|---|---|---|---|
| AAA | GTG | TAT | GGC | CGC | TGC | CGG | ATG | GAG | AAA | GAA | GAG | GAT | TTG | TGG | GGC | 676 |
| Lys | Val | Tyr | Gly | Arg | Cys | Arg | Met | Glu | Lys | Glu | Glu | Asp | Leu | Trp | Gly | |
| | | 205 | | | | | 210 | | | | | 215 | | | | |

```
AAA GTG TAT GGC CGC TGC CGG ATG GAG AAA GAA GAG GAT TTG TGG GGC        676
Lys Val Tyr Gly Arg Cys Arg Met Glu Lys Glu Glu Asp Leu Trp Gly
        205                 210                 215

GAG TGG AGC CCC ATT TTG TCC TTC CAG ACA CCG CCT TCT GCT CCA AAA        724
Glu Trp Ser Pro Ile Leu Ser Phe Gln Thr Pro Pro Ser Ala Pro Lys
    220                 225                 230

GAT GTG TGG GTA TCA GGG AAC CTC TGT GGG ACG CCT GGA GGA GAG GAA        772
Asp Val Trp Val Ser Gly Asn Leu Cys Gly Thr Pro Gly Gly Glu Glu
235                 240                 245                 250

CCT TTG CTT CTA TGG AAG GCC CCA GGG CCC TGT GTG CAG GTG AGC TAC        820
Pro Leu Leu Leu Trp Lys Ala Pro Gly Pro Cys Val Gln Val Ser Tyr
                255                 260                 265

AAA GTC TGG TTC TGG GTT GGA GGT CGT GAG CTG AGT CCA GAA GGA ATT        868
Lys Val Trp Phe Trp Val Gly Gly Arg Glu Leu Ser Pro Glu Gly Ile
            270                 275                 280

ACC TGC TGC TGC TCC CTA ATT CCC AGT GGG GCG GAG TGG GCC AGG GTG        916
Thr Cys Cys Cys Ser Leu Ile Pro Ser Gly Ala Glu Trp Ala Arg Val
        285                 290                 295

TCC GCT GTC AAC GCC ACA AGC TGG GAG CCT CTC ACC AAC CTC TCT TTG        964
Ser Ala Val Asn Ala Thr Ser Trp Glu Pro Leu Thr Asn Leu Ser Leu
    300                 305                 310

GTC TGC TTG GAT TCA GCC TCT GCC CCC CGT AGC GTG GCA GTC AGC AGC       1012
Val Cys Leu Asp Ser Ala Ser Ala Pro Arg Ser Val Ala Val Ser Ser
315                 320                 325                 330

ATC GCT GGG AGC ACG GAG CTA CTG GTG ACC TGG CAA CCG GGG CCT GGG       1060
Ile Ala Gly Ser Thr Glu Leu Leu Val Thr Trp Gln Pro Gly Pro Gly
                335                 340                 345

GAA CCA CTG GAG CAT GTA GTG GAC TGG GCT CGA GAT GGG GAC CCC CTG       1108
Glu Pro Leu Glu His Val Val Asp Trp Ala Arg Asp Gly Asp Pro Leu
            350                 355                 360

GAG AAA CTC AAC TGG GTC CGG CTT CCC CCT GGG AAC CTC AGT GCT CTG       1156
Glu Lys Leu Asn Trp Val Arg Leu Pro Pro Gly Asn Leu Ser Ala Leu
        365                 370                 375

TTA CCA GGG AAT TTC ACT GTC GGG GTC CCC TAT CGA ATC ACT GTG ACC       1204
Leu Pro Gly Asn Phe Thr Val Gly Val Pro Tyr Arg Ile Thr Val Thr
    380                 385                 390

GCA GTC TCT GCT TCA GGC TTG GCC TCT GCA TCC TCC GTC TGG GGG TTC       1252
Ala Val Ser Ala Ser Gly Leu Ala Ser Ala Ser Ser Val Trp Gly Phe
395                 400                 405                 410

AGG GAG GAA TTA GCA CCC CTA GTG GGG CCA ACG CTT TGG CGA CTC CAA       1300
Arg Glu Glu Leu Ala Pro Leu Val Gly Pro Thr Leu Trp Arg Leu Gln
                415                 420                 425

GAT GCC CCT CCA GGG ACC CCC GCC ATA GCG TGG GGA GAG GTC CCA AGG       1348
Asp Ala Pro Pro Gly Thr Pro Ala Ile Ala Trp Gly Glu Val Pro Arg
            430                 435                 440

CAC CAG CTT CGA GGC CAC CTC ACC CAC TAC ACC TTG TGT GCA CAG AGT       1396
His Gln Leu Arg Gly His Leu Thr His Tyr Thr Leu Cys Ala Gln Ser
        445                 450                 455

GGA ACC AGC CCC TCC GTC TGC ATG AAT GTG AGT GGC AAC ACA CAG AGT       1444
Gly Thr Ser Pro Ser Val Cys Met Asn Val Ser Gly Asn Thr Gln Ser
    460                 465                 470

GTC ACC CTG CCT GAC CTT CCT TGG GGT CCC TGT GAG CTG TGG GTG ACA       1492
Val Thr Leu Pro Asp Leu Pro Trp Gly Pro Cys Glu Leu Trp Val Thr
475                 480                 485                 490

GCA TCT ACC ATC GCT GGA CAG GGC CCT CCT GGT CCC ATC CTC CGG CTT       1540
Ala Ser Thr Ile Ala Gly Gln Gly Pro Pro Gly Pro Ile Leu Arg Leu
                495                 500                 505

CAT CTA CCA GAT AAC ACC CTG AGG TGG AAA GTT CTG CCG GGC ATC CTA       1588
His Leu Pro Asp Asn Thr Leu Arg Trp Lys Val Leu Pro Gly Ile Leu
```

```
                510              515              520
TTC TTG TGG GGC TTG TTC CTG TTG GGG TGT GGC CTG AGC CTG GCC ACC      1636
Phe Leu Trp Gly Leu Phe Leu Leu Gly Cys Gly Leu Ser Leu Ala Thr
            525                  530                  535

TCT GGA AGG TGC TAC CAC CTA AGG CAC AAA GTA CTG CCC CGC TGG GTC      1684
Ser Gly Arg Cys Tyr His Leu Arg His Lys Val Leu Pro Arg Trp Val
            540                  545                  550

TGG GAG AAA GTT CCT GAT CCT GCC AAC AGC AGT TCA GGC CTT CTG GGG      1732
Trp Glu Lys Val Pro Asp Pro Ala Asn Ser Ser Ser Gly Leu Leu Gly
555                  560                  565                  570

CCC CCC AGG CCA CAG GTT CTG GCC TGAACCACAC GTCTGGCTGG GGGCTGCCAG     1786
Pro Pro Arg Pro Gln Val Leu Ala
                575

CCAGGCTAGA GGGATGCTCA TGCAGGTTGC ACCCCAGTCC TGGATTAGCC CTCTTGATGG    1846

ATGAAGACAC TGAGGACTCA GAGAGGCTGA GTCACTTACC TGAGGACACC CAGCCAGGCA    1906

GAGCTGGGAT TGAAGGACCC CTATAGAGAA GGGCTTGGCC CCCATGGGGA AGACACGGAT    1966

GGAAGGTGGA GCAAAGGAAA ATACATGAAA TTGAGAGTGG CAGCTGCCTG CCAAAATCTG    2026

TTCCGCTGTA ACAGAACTGA ATTTGGACCC CAGCCAGTGG CTCACGCCTG TAATCCCAGC    2086

ACTTTGGCAG GCCAAGGTGG AAGGATCACT TAGAGCTAGG AGTTTGAGAC CAGCCTGGGC    2146

AATATGCAAG ACCCCTCACT ACAAAAATAA AACATCAAAA ACAAAAACAA TTAGCTGGGC    2206

ATGATGGCAC ACACCTGTGT CCAGCCACT TGGGAGGCTG GGTGGGAGGA TCGGTTGAGC     2266

CCAGGAGTTC GAAGCTGCAG GGACCTCTGA TTGCACCACT GCACTCCAGG CTGGGTAACA    2326

GAATGAGCCT TATCTCAAAA ATAAACAAAC TAATAAAAAG TA                       2368

(2) INFORMATION FOR SEQ ID NO:3:

(i) SEQUENCE CHARACTERISTICS:
         (A) LENGTH: 578 amino acids
         (B) TYPE: amino acid
         (D) TOPOLOGY: linear (ii) MOLECULE TYPE: protein (xi) SEQUENCE DESCRIPTION: SEQ ID NO:3:

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
                20                  25                  30

Gln Gly Ser Ala Gly Pro Leu Gln Cys Tyr Gly Val Gly Pro Leu Gly
            35                  40                  45

Asp Leu Asn Cys Ser Trp Glu Pro Leu Gly Asp Leu Gly Ala Pro Ser
        50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Pro Thr Trp Pro Ser His Lys
```

-continued

```
                145                 150                 155                 160
Val Leu Ile Cys Gln Phe His Tyr Arg Arg Cys Gln Glu Ala Ala Trp
                    165                 170                 175

Thr Leu Leu Glu Pro Glu Leu Lys Thr Ile Pro Leu Thr Pro Val Glu
                    180                 185                 190

Ile Gln Asp Leu Glu Leu Ala Thr Gly Tyr Lys Val Tyr Gly Arg Cys
                    195                 200                 205

Arg Met Glu Lys Glu Glu Asp Leu Trp Gly Glu Trp Ser Pro Ile Leu
                    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                    245                 250                 255

Ala Pro Gly Pro Cys Val Gln Val Ser Tyr Lys Val Trp Phe Trp Val
                    260                 265                 270

Gly Gly Arg Glu Leu Ser Pro Glu Gly Ile Thr Cys Cys Cys Ser Leu
                    275                 280                 285

Ile Pro Ser Gly Ala Glu Trp Ala Arg Val Ser Ala Val Asn Ala Thr
                    290                 295                 300

Ser Trp Glu Pro Leu Thr Asn Leu Ser Leu Val Cys Leu Asp Ser Ala
305                 310                 315                 320

Ser Ala Pro Arg Ser Val Ala Val Ser Ser Ile Ala Gly Ser Thr Glu
                    325                 330                 335

Leu Leu Val Thr Trp Gln Pro Gly Pro Gly Glu Pro Leu Glu His Val
                    340                 345                 350

Val Asp Trp Ala Arg Asp Gly Asp Pro Leu Glu Lys Leu Asn Trp Val
                    355                 360                 365

Arg Leu Pro Pro Gly Asn Leu Ser Ala Leu Leu Pro Gly Asn Phe Thr
                    370                 375                 380

Val Gly Val Pro Tyr Arg Ile Thr Val Thr Ala Val Ser Ala Ser Gly
385                 390                 395                 400

Leu Ala Ser Ala Ser Ser Val Trp Gly Phe Arg Glu Glu Leu Ala Pro
                    405                 410                 415

Leu Val Gly Pro Thr Leu Trp Arg Leu Gln Asp Ala Pro Pro Gly Thr
                    420                 425                 430

Pro Ala Ile Ala Trp Gly Glu Val Pro Arg His Gln Leu Arg Gly His
                    435                 440                 445

Leu Thr His Tyr Thr Leu Cys Ala Gln Ser Gly Thr Ser Pro Ser Val
                    450                 455                 460

Cys Met Asn Val Ser Gly Asn Thr Gln Ser Val Thr Leu Pro Asp Leu
465                 470                 475                 480

Pro Trp Gly Pro Cys Glu Leu Trp Val Thr Ala Ser Thr Ile Ala Gly
                    485                 490                 495

Gln Gly Pro Pro Gly Pro Ile Leu Arg Leu His Leu Pro Asp Asn Thr
                    500                 505                 510

Leu Arg Trp Lys Val Leu Pro Gly Ile Leu Phe Leu Trp Gly Leu Phe
                    515                 520                 525

Leu Leu Gly Cys Gly Leu Ser Leu Ala Thr Ser Gly Arg Cys Tyr His
                    530                 535                 540

Leu Arg His Lys Val Leu Pro Arg Trp Val Trp Glu Lys Val Pro Asp
545                 550                 555                 560

Pro Ala Asn Ser Ser Gly Leu Leu Gly Pro Pro Arg Pro Gln Val
                    565                 570                 575
```

Leu Ala (2) INFORMATION FOR SEQ ID NO:4:

(i) SEQUENCE CHARACTERISTICS:
        (A) LENGTH: 2663 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 139..2049

(xi) SEQUENCE DESCRIPTION: SEQ ID NO:4:

```
ACGAGGCGGA GGCGGCCTGC CGGGGTGGTT CGGCTTCCCG TTGCCGCCTC GGGCGCTGTA      60

CCCAGAGCTC GAAGAGGAGC AGCGCGGCCG CGCGGACCCG GCAAGGCTGG GCCGGACTCG     120

GGGCTCCCGA GGGACGCC ATG CGG GGA GGC AGG GGC GCC CCT TTC TGG CTG      171
                    Met Arg Gly Gly Arg Gly Ala Pro Phe Trp Leu
                     1               5                  10

TGG CCG CTG CCC AAG CTG GCG CTG CTG CCT CTG TTG TGG GTG CTT TTC      219
Trp Pro Leu Pro Lys Leu Ala Leu Leu Pro Leu Leu Trp Val Leu Phe
             15                  20                  25

CAG CGG ACG CGT CCC CAG GGC AGC GCC GGG CCA CTG CAG TGC TAC GGA      267
Gln Arg Thr Arg Pro Gln Gly Ser Ala Gly Pro Leu Gln Cys Tyr Gly
         30                  35                  40

GTT GGA CCC TTG GGC GAC TTG AAC TGC TCG TGG GAG CCT CTT GGG GAC      315
Val Gly Pro Leu Gly Asp Leu Asn Cys Ser Trp Glu Pro Leu Gly Asp
     45                  50                  55

CTG GGA GCC CCC TCC GAG TTA CAC CTC CAG AGC CAA AAG TAC CGT TCC      363
Leu Gly Ala Pro Ser Glu Leu His Leu Gln Ser Gln Lys Tyr Arg Ser
 60                  65                  70                  75

AAC AAA ACC CAG ACT GTG GCA GTG GCA GCC GGA CGG AGC TGG GTG GCC      411
Asn Lys Thr Gln Thr Val Ala Val Ala Ala Gly Arg Ser Trp Val Ala
             80                  85                  90

ATT CCT CGG GAA CAG CTC ACC ATG TCT GAC AAA CTC CTT GTC TGG GGC      459
Ile Pro Arg Glu Gln Leu Thr Met Ser Asp Lys Leu Leu Val Trp Gly
         95                  100                 105

ACT AAG GCA GGC CAG CCT CTC TGG CCC CCC GTC TTC GTG AAC CTA GAA      507
Thr Lys Ala Gly Gln Pro Leu Trp Pro Pro Val Phe Val Asn Leu Glu
     110                 115                 120

ACC CAA ATG AAG CCA AAC GCC CCC CGG CTG GGC CCT GAC GTG GAC TTT      555
Thr Gln Met Lys Pro Asn Ala Pro Arg Leu Gly Pro Asp Val Asp Phe
 125                 130                 135

TCC GAG GAT GAC CCC CTG GAG GCC ACT GTC CAT TGG GCC CCA CCT ACA      603
Ser Glu Asp Asp Pro Leu Glu Ala Thr Val His Trp Ala Pro Pro Thr
140                 145                 150                 155

TGG CCA TCT CAT AAA GTT CTG ATC TGC CAG TTC CAC TAC CGA AGA TGT      651
Trp Pro Ser His Lys Val Leu Ile Cys Gln Phe His Tyr Arg Arg Cys
             160                 165                 170

CAG GAG GCG GCC TGG ACC CTG CTG GAA CCG GAG CTG AAG ACC ATA CCC      699
Gln Glu Ala Ala Trp Thr Leu Leu Glu Pro Glu Leu Lys Thr Ile Pro
         175                 180                 185

CTG ACC CCT GTT GAG ATC CAA GAT TTG GAG CTA GCC ACT GGC TAC AAA      747
Leu Thr Pro Val Glu Ile Gln Asp Leu Glu Leu Ala Thr Gly Tyr Lys
     190                 195                 200

GTG TAT GGC CGC TGC CGG ATG GAG AAA GAA GAG GAT TTG TGG GGC GAG      795
```

-continued

```
                Val Tyr Gly Arg Cys Arg Met Glu Lys Glu Glu Asp Leu Trp Gly Glu
                205                 210                 215

TGG AGC CCC ATT TTG TCC TTC CAG ACA CCG CCT TCT GCT CCA AAA GAT       843
Trp Ser Pro Ile Leu Ser Phe Gln Thr Pro Pro Ser Ala Pro Lys Asp
220                 225                 230                 235

GTG TGG GTA TCA GGG AAC CTC TGT GGG ACG CCT GGA GGA GAG GAA CCT       891
Val Trp Val Ser Gly Asn Leu Cys Gly Thr Pro Gly Gly Glu Glu Pro
                    240                 245                 250

TTG CTT CTA TGG AAG GCC CCA GGG CCC TGT GTG CAG GTG AGC TAC AAA       939
Leu Leu Leu Trp Lys Ala Pro Gly Pro Cys Val Gln Val Ser Tyr Lys
                255                 260                 265

GTC TGG TTC TGG GTT GGA GGT CGT GAG CTG AGT CCA GAA GGA ATT ACC       987
Val Trp Phe Trp Val Gly Gly Arg Glu Leu Ser Pro Glu Gly Ile Thr
            270                 275                 280

TGC TGC TGC TCC CTA ATT CCC AGT GGG GCG GAG TGG GCC AGG GTG TCC      1035
Cys Cys Cys Ser Leu Ile Pro Ser Gly Ala Glu Trp Ala Arg Val Ser
285                 290                 295

GCT GTC AAC GCC ACA AGC TGG GAG CCT CTC ACC AAC CTC TCT TTG GTC      1083
Ala Val Asn Ala Thr Ser Trp Glu Pro Leu Thr Asn Leu Ser Leu Val
300                 305                 310                 315

TGC TTG GAT TCA GCC TCT GCC CCC CGT AGC GTG GCA GTC AGC AGC ATC      1131
Cys Leu Asp Ser Ala Ser Ala Pro Arg Ser Val Ala Val Ser Ser Ile
                320                 325                 330

GCT GGG AGC ACG GAG CTA CTG GTG ACC TGG CAA CCG GGG CCT GGG GAA      1179
Ala Gly Ser Thr Glu Leu Leu Val Thr Trp Gln Pro Gly Pro Gly Glu
                335                 340                 345

CCA CTG GAG CAT GTA GTG GAC TGG GCT CGA GAT GGG GAC CCC CTG GAG      1227
Pro Leu Glu His Val Val Asp Trp Ala Arg Asp Gly Asp Pro Leu Glu
                350                 355                 360

AAA CTC AAC TGG GTC CGG CTT CCC CCT GGG AAC CTC AGT GCT CTG TTA      1275
Lys Leu Asn Trp Val Arg Leu Pro Pro Gly Asn Leu Ser Ala Leu Leu
365                 370                 375

CCA GGG AAT TTC ACT GTC GGG GTC CCC TAT CGA ATC ACT GTG ACC GCA      1323
Pro Gly Asn Phe Thr Val Gly Val Pro Tyr Arg Ile Thr Val Thr Ala
380                 385                 390                 395

GTC TCT GCT TCA GGC TTG GCC TCT GCA TCC TCC GTC TGG GGG TTC AGG      1371
Val Ser Ala Ser Gly Leu Ala Ser Ala Ser Ser Val Trp Gly Phe Arg
                400                 405                 410

GAG GAA TTA GCA CCC CTA GTG GGG CCA ACG CTT TGG CGA CTC CAA GAT      1419
Glu Glu Leu Ala Pro Leu Val Gly Pro Thr Leu Trp Arg Leu Gln Asp
                415                 420                 425

GCC CCT CCA GGG ACC CCC GCC ATA GCG TGG GGA GAG GTC CCA AGG CAC      1467
Ala Pro Pro Gly Thr Pro Ala Ile Ala Trp Gly Glu Val Pro Arg His
                430                 435                 440

CAG CTT CGA GGC CAC CTC ACC CAC TAC ACC TTG TGT GCA CAG AGT GGA      1515
Gln Leu Arg Gly His Leu Thr His Tyr Thr Leu Cys Ala Gln Ser Gly
                445                 450                 455

ACC AGC CCC TCC GTC TGC ATG AAT GTG AGT GGC AAC ACA CAG AGT GTC      1563
Thr Ser Pro Ser Val Cys Met Asn Val Ser Gly Asn Thr Gln Ser Val
460                 465                 470                 475

ACC TGC CCT GAC CTT CCT TGG GGT CCC TGT GAG CTG TGG GTG ACA GCA      1611
Thr Leu Pro Asp Leu Pro Trp Gly Pro Cys Glu Leu Trp Val Thr Ala
                480                 485                 490

TCT ACC ATC GCT GGA CAG GGC CCT CCT GGT CCC ATC CTC CGG CTT CAT      1659
Ser Thr Ile Ala Gly Gln Gly Pro Pro Gly Pro Ile Leu Arg Leu His
                495                 500                 505

CTA CCA GAT AAC ACC CTG AGG TGG AAA GTT CTG CCA GGC ATC CTA TTC      1707
Leu Pro Asp Asn Thr Leu Arg Trp Lys Val Leu Pro Gly Ile Leu Phe
```

```
                510                 515                 520
TTG TGG GGC TTG TTC CTG TTG GGG TGT GGC CTG AGC CTG GCC ACC TCT      1755
Leu Trp Gly Leu Phe Leu Leu Gly Cys Gly Leu Ser Leu Ala Thr Ser
    525                 530                 535

GGA AGG TGC TAC CAC CTA AGG CAC AAA GTG CTG CCC CGC TGG GTC TGG      1803
Gly Arg Cys Tyr His Leu Arg His Lys Val Leu Pro Arg Trp Val Trp
540                 545                 550                 555

GAG AAA GTT CCT GAT CCT GCC AAC AGC AGT TCA GGC CAG CCC CAC ATG      1851
Glu Lys Val Pro Asp Pro Ala Asn Ser Ser Ser Gly Gln Pro His Met
                560                 565                 570

GAG CAA GTA CCT GAG GCC CAG CCC CTT GGG GAC TTG CCC ATC CTG GAA      1899
Glu Gln Val Pro Glu Ala Gln Pro Leu Gly Asp Leu Pro Ile Leu Glu
            575                 580                 585

GTG GAG GAG ATG GAG CCC CCG CCG GTT ATG GAG TCC TCC CAG CCC GCC      1947
Val Glu Glu Met Glu Pro Pro Pro Val Met Glu Ser Ser Gln Pro Ala
        590                 595                 600

CAG GCC ACC GCC CCG CTT GAC TCT GGG TAT GAG AAG CAC TTC CTG CCC      1995
Gln Ala Thr Ala Pro Leu Asp Ser Gly Tyr Glu Lys His Phe Leu Pro
    605                 610                 615

ACA CCT GAG GAG CTG GGC CTT CTG GGG CCC CCC AGG CCA CAG GTT CTG      2043
Thr Pro Glu Glu Leu Gly Leu Leu Gly Pro Pro Arg Pro Gln Val Leu
620                 625                 630                 635

GCC TGAACCACAC GTCTGGCTGG GGGCTGCCAG CCAGGCTAGA GGGATGCTCA           2096
Ala

TGCAGGTTGC ACCCCAGTCC TGGATTAGCC CTCTTGATGG ATGAAGACAC TGAGGACTCA    2156

GAGAGGCTGA GTCACTTACC TGAGGACACC CAGCCAGGCA GAGCTGGGAT TGAAGGACCC    2216

CTATAGAGAA GGGCTTGGCC CCCATGGGGA AGACACGGAT GGAAGGTGGA GCAAAGGAAA    2276

ATACATGAAA TTGAGAGTGG CAGCTGCCTG CCAAAATCTG TTCCGCTGTA ACAGAACTGA    2336

ATTTGGACCC CAGCACAGTG GCTCACGCCT GTAATCCCAG CACTTTGGCA GGCCAAGGTG    2396

GAAGGATCAC TTAGAGCTAG GAGTTTGAGA CCAGCCTGGG CAATATAGCA AGACCCCTCA    2456

CTACAAAAAT AAAACATCAA AAACAAAAAC AATTAGCTGG GCATGATGGC ACACACCTGT    2516

AGTCCGAGCC ACTTGGGAGG CTGAGGTGGG AGGATCGGTT GAGCCCAGGA GTTCGAAGCT    2576

GCAGGGACCT CTGATTGCAC CACTGCACTC CAGGCTGGGT AACAGAATGA GACCTTATCT    2636

CAAAAATAAA CAAACTAATA AAAAGCA                                        2663

(2) INFORMATION FOR SEQ ID NO:5:

(i) SEQUENCE CHARACTERISTICS:
        (A) LENGTH: 636 amino acids
        (B) TYPE: amino acid
        (D) TOPOLOGY: linear (ii) MOLECULE TYPE: protein (xi) SEQUENCE DESCRIPTION: SEQ ID NO:5:

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
```

```
                65                  70                  75                  80
Val Ala Val Ala Ala Gly Arg Ser Trp Val Ala Ile Pro Arg Glu Gln
                        85                  90                  95
Leu Thr Met Ser Asp Lys Leu Leu Val Trp Gly Thr Lys Ala Gly Gln
                100                 105                 110
Pro Leu Trp Pro Pro Val Phe Val Asn Leu Glu Thr Gln Met Lys Pro
            115                 120                 125
Asn Ala Pro Arg Leu Gly Pro Asp Val Asp Phe Ser Glu Asp Asp Pro
130                 135                 140
Leu Glu Ala Thr Val His Trp Ala Pro Thr Trp Pro Ser His Lys
145                 150                 155                 160
Val Leu Ile Cys Gln Phe His Tyr Arg Arg Cys Gln Glu Ala Ala Trp
                165                 170                 175
Thr Leu Leu Glu Pro Glu Leu Lys Thr Ile Pro Leu Thr Pro Val Glu
                180                 185                 190
Ile Gln Asp Leu Glu Leu Ala Thr Gly Tyr Lys Val Tyr Gly Arg Cys
            195                 200                 205
Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240
Asn Leu Cys Gly Thr Pro Gly Gly Glu Glu Pro Leu Leu Leu Trp Lys
                245                 250                 255
Ala Pro Gly Pro Cys Val Gln Val Ser Tyr Lys Val Trp Phe Trp Val
                260                 265                 270
Gly Gly Arg Glu Leu Ser Pro Glu Gly Ile Thr Cys Cys Ser Leu
            275                 280                 285
Ile Pro Ser Gly Ala Glu Trp Ala Arg Val Ser Ala Val Asn Ala Thr
    290                 295                 300
Ser Trp Glu Pro Leu Thr Asn Leu Ser Leu Val Cys Leu Asp Ser Ala
305                 310                 315                 320
Ser Ala Pro Arg Ser Val Ala Val Ser Ser Ile Ala Gly Ser Thr Glu
                325                 330                 335
Leu Leu Val Thr Trp Gln Pro Gly Pro Gly Glu Pro Leu Glu His Val
                340                 345                 350
Val Asp Trp Ala Arg Asp Gly Asp Pro Leu Glu Lys Leu Asn Trp Val
            355                 360                 365

Arg Leu Pro Pro Gly Asn Leu Ser Ala Leu Leu Pro Gly Asn Phe Thr
    370                 375                 380
Val Gly Val Pro Tyr Arg Ile Thr Val Thr Ala Val Ser Ala Ser Gly
385                 390                 395                 400
Leu Ala Ser Ala Ser Ser Val Trp Gly Phe Arg Glu Glu Leu Ala Pro
                405                 410                 415
Leu Val Gly Pro Thr Leu Trp Arg Leu Gln Asp Ala Pro Pro Gly Thr
                420                 425                 430
Pro Ala Ile Ala Trp Gly Glu Val Pro Arg His Gln Leu Arg Gly His
            435                 440                 445
Leu Thr His Tyr Thr Leu Cys Ala Gln Ser Gly Thr Ser Pro Ser Val
    450                 455                 460
Cys Met Asn Val Ser Gly Asn Thr Gln Ser Val Thr Leu Pro Asp Leu
465                 470                 475                 480
```

```
Pro Trp Gly Pro Cys Glu Leu Trp Val Thr Ala Ser Thr Ile Ala Gly
                485                 490                 495

Gln Gly Pro Pro Gly Pro Ile Leu Arg Leu His Leu Pro Asp Asn Thr
                500                 505                 510

Leu Arg Trp Lys Val Leu Pro Gly Ile Leu Phe Leu Trp Gly Leu Phe
                515                 520                 525

Leu Leu Gly Cys Gly Leu Ser Leu Ala Thr Ser Gly Arg Cys Tyr His
        530                 535                 540

Leu Arg His Lys Val Leu Pro Arg Trp Val Trp Glu Lys Val Pro Asp
545                 550                 555                 560

Pro Ala Asn Ser Ser Gly Gln Pro His Met Glu Gln Val Pro Glu
                565                 570                 575

Ala Gln Pro Leu Gly Asp Leu Pro Ile Leu Glu Val Glu Glu Met Glu
                580                 585                 590

Pro Pro Pro Val Met Glu Ser Ser Gln Pro Ala Gln Ala Thr Ala Pro
                595                 600                 605

Leu Asp Ser Gly Tyr Glu Lys His Phe Leu Pro Thr Pro Glu Glu Leu
            610                 615                 620

Gly Leu Leu Gly Pro Pro Arg Pro Gln Val Leu Ala
625                 630                 635

(2) INFORMATION FOR SEQ ID NO:6:

(i) SEQUENCE CHARACTERISTICS:
        (A) LENGTH: 2589 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 11..1882

(xi) SEQUENCE DESCRIPTION: SEQ ID NO:6:

GCTGGGAGCC ATG AAC CGG CTC CGG GTT GCA CGC CTC ACG CCG TTG GAG        49
           Met Asn Arg Leu Arg Val Ala Arg Leu Thr Pro Leu Glu
            1               5                  10

CTT CTG CTG TCG CTG ATG TCG CTG CTC GGG ACG CGG CCC CAC GGC           97
Leu Leu Leu Ser Leu Met Ser Leu Leu Leu Gly Thr Arg Pro His Gly
 15                  20                  25

AGT CCA GGC CCA CTG CAG TGC TAC AGC GTC GGT CCC CTG GGA ATC CTG      145
Ser Pro Gly Pro Leu Gln Cys Tyr Ser Val Gly Pro Leu Gly Ile Leu
 30                  35                  40                  45

AAC TGC TCC TGG GAA CCT TTG GGC GAC CTG GAG ACT CCA CCT GTG CTG      193
Asn Cys Ser Trp Glu Pro Leu Gly Asp Leu Glu Thr Pro Pro Val Leu
                 50                  55                  60

TAT CAC CAG AGT CAG AAA TAC CAT CCC AAT AGA GTC TGG GAG GTG AAG      241
Tyr His Gln Ser Gln Lys Tyr His Pro Asn Arg Val Trp Glu Val Lys
             65                  70                  75

GTG CCT TCC AAA CAG AGT TGG GTG ACC ATT CCC CGG GAA CAG TTC ACC      289
Val Pro Ser Lys Gln Ser Trp Val Thr Ile Pro Arg Glu Gln Phe Thr
         80                  85                  90

ATG GCT GAC AAA CTC CTC ATC TGG GGG ACA CAA AAG GGA CGG CCT CTG      337
Met Ala Asp Lys Leu Leu Ile Trp Gly Thr Gln Lys Gly Arg Pro Leu
     95                 100                 105

TGG TCC TCT GTC TCT GTG AAC CTG GAG ACC CAA ATG AAG CCA GAC ACA      385
Trp Ser Ser Val Ser Val Asn Leu Glu Thr Gln Met Lys Pro Asp Thr
110                 115                 120                 125
```

-continued

| | | |
|---|---|---|
| CCT CAG ATC TTC TCT CAA GTG GAT ATT TCT GAG GAA GCA ACC CTG GAG<br>Pro Gln Ile Phe Ser Gln Val Asp Ile Ser Glu Glu Ala Thr Leu Glu<br>130                           135                         140 | 433 | |
| GCC ACT GTG CAG TGG GCG CCG CCC GTG TGG CCA CCG CAG AAA GCT CTC<br>Ala Thr Val Gln Trp Ala Pro Pro Val Trp Pro Pro Gln Lys Ala Leu<br>             145                         150                        155 | 481 | |
| ACC TGT CAG TTC CGG TAC AAG GAA TGC CAG GCT GAA GCA TGG ACC CGG<br>Thr Cys Gln Phe Arg Tyr Lys Glu Cys Gln Ala Glu Ala Trp Thr Arg<br>             160                         165                        170 | 529 | |
| CTG GAG CCC CAG CTG AAG ACA GAT GGG CTG ACT CCT GTT GAG ATG CAG<br>Leu Glu Pro Gln Leu Lys Thr Asp Gly Leu Thr Pro Val Glu Met Gln<br>175                           180                         185 | 577 | |
| AAC CTG GAA CCT GGC ACC TGC TAC CAG GTG TCT GGC CGC TGC CAG GTG<br>Asn Leu Glu Pro Gly Thr Cys Tyr Gln Val Ser Gly Arg Cys Gln Val<br>190                           195                         200                        205 | 625 | |
| GAG AAC GGA TAT CCA TGG GGC GAG TGG AGT TCG CCC CTG TCC TTC CAG<br>Glu Asn Gly Tyr Pro Trp Gly Glu Trp Ser Ser Pro Leu Ser Phe Gln<br>             210                         215                        220 | 673 | |
| ACG CCA TTC TTA GAT CCT GAA GAT GTG TGG GTA TCG GGG ACC GTC TGT<br>Thr Pro Phe Leu Asp Pro Glu Asp Val Trp Val Ser Gly Thr Val Cys<br>             225                         230                        235 | 721 | |
| GAA ACT TCT GGC AAA CGG GCA GCC CTG CTT GTC TGG AAG GAC CCA AGA<br>Glu Thr Ser Gly Lys Arg Ala Ala Leu Leu Val Trp Lys Asp Pro Arg<br>             240                         245                        250 | 769 | |
| CCT TGT GTG CAG GTG ACT TAC ACA GTC TGG TTT GGG GCT GGA GAT ATT<br>Pro Cys Val Gln Val Thr Tyr Thr Val Trp Phe Gly Ala Gly Asp Ile<br>255                           260                         265 | 817 | |
| ACT ACA ACT CAA GAA GAG GTC CCG TGC TGC AAG TCC CCT GTC CCT GCA<br>Thr Thr Thr Gln Glu Glu Val Pro Cys Cys Lys Ser Pro Val Pro Ala<br>270                           275                         280                        285 | 865 | |
| TGG ATG GAG TGG GCT GTG GTC TCT CCT GGC AAC AGC ACC AGC TGG GTG<br>Trp Met Glu Trp Ala Val Val Ser Pro Gly Asn Ser Thr Ser Trp Val<br>                      290                         295                        300 | 913 | |
| CCT CCC ACC AAC CTG TCT CTG GTG TGC TTG GCT CCA GAA TCT GCC CCC<br>Pro Pro Thr Asn Leu Ser Leu Val Cys Leu Ala Pro Glu Ser Ala Pro<br>                      305                         310                        315 | 961 | |
| TGT GAC GTG GGA GTG AGC AGT GCT GAT GGG AGC CCA GGG ATA AAG GTG<br>Cys Asp Val Gly Val Ser Ser Ala Asp Gly Ser Pro Gly Ile Lys Val<br>                      320                         325                        330 | 1009 | |
| ACC TGG AAA CAA GGG ACC AGG AAA CCA TTG GAG TAT GTG GTG GAC TGG<br>Thr Trp Lys Gln Gly Thr Arg Lys Pro Leu Glu Tyr Val Val Asp Trp<br>335                           340                         345 | 1057 | |
| GCT CAA GAT GGT GAC AGC CTG GAC AAG CTC AAC TGG ACC CGT CTC CCC<br>Ala Gln Asp Gly Asp Ser Leu Asp Lys Leu Asn Trp Thr Arg Leu Pro<br>350                           355                         360                        365 | 1105 | |
| CCT GGA AAC CTC AGC ACA TTG TTA CCA GGG GAG TTC AAA GGA GGG TA<br>Pro Gly Asn Leu Ser Thr Leu Leu Pro Gly Glu Phe Lys Gly Gly Val<br>                      370                         375                        380 | 1153 | |
| CCC TAT CGA ATT ACA GTG ACT GCA GTA TAC TCT GGA GGA TTA GCT GCT<br>Pro Tyr Arg Ile Thr Val Thr Ala Val Tyr Ser Gly Gly Leu Ala Ala<br>                      385                         390                        395 | 1201 | |
| GCA CCC TCA GTT TGG GGA TTC AGA GAG GAG TTA GTA CCC CTT GCT GGG<br>Ala Pro Ser Val Trp Gly Phe Arg Glu Glu Leu Val Pro Leu Ala Gly<br>                      400                         405                        410 | 1249 | |
| CCA GCA GTT TGG CGA CTT CCA GAT GAC CCC CCA GGG ACA CCT GTT GTA<br>Pro Ala Val Trp Arg Leu Pro Asp Asp Pro Pro Gly Thr Pro Val Val<br>415                           420                         425 | 1297 | |
| GCC TGG GGA GAA GTA CCA AGA CAC CAG CTC AGA GGC CAG GCT ACT CAC | 1345 | |

-continued

```
Ala Trp Gly Glu Val Pro Arg His Gln Leu Arg Gly Gln Ala Thr His
430                 435                 440                 445

TAC ACC TTC TGC ATA CAG AGC AGA GGC CTC TCC ACT GTC TGC AGG AAC     1393
Tyr Thr Phe Cys Ile Gln Ser Arg Gly Leu Ser Thr Val Cys Arg Asn
                450                 455                 460

GTG AGC AGT CAA ACC CAG ACT GCC ACT CTG CCC AAC CTT CAC TCG GGT     1441
Val Ser Ser Gln Thr Gln Thr Ala Thr Leu Pro Asn Leu His Ser Gly
                465                 470                 475

TCC TTC AAG CTG TGG GTG ACG GTG TCC ACC GTT GCA GGA CAG GGC CCA     1489
Ser Phe Lys Leu Trp Val Thr Val Ser Thr Val Ala Gly Gln Gly Pro
                480                 485                 490

CCT GGT CCC GAC CTT TCA CTT CAC CTA CCA GAT AAT AGG ATC AGG TGG     1537
Pro Gly Pro Asp Leu Ser Leu His Leu Pro Asp Asn Arg Ile Arg Trp
495                 500                 505

AAA GCT CTG CCC TGG TTT CTG TCC CTG TGG GGT TTG CTT CTG ATG GGC     1585
Lys Ala Leu Pro Trp Phe Leu Ser Leu Trp Gly Leu Leu Leu Met Gly
510                 515                 520                 525

TGT GGC CTG AGC CTG GCC AGT ACC AGG TGC CTA CAG GCC AGG TGC TTA     1633
Cys Gly Leu Ser Leu Ala Ser Thr Arg Cys Leu Gln Ala Arg Cys Leu
                530                 535                 540

CAC TGG CGA CAC AAG TTG CTT CCC CAG TGG ATC TGG GAG AGG GTT CCT     1681
His Trp Arg His Lys Leu Leu Pro Gln Trp Ile Trp Glu Arg Val Pro
                545                 550                 555

GAT CCT GCC AAC AGC AAT TCT GGG CAA CCT TAC ATC AAG GAG GTG AGC     1729
Asp Pro Ala Asn Ser Asn Ser Gly Gln Pro Tyr Ile Lys Glu Val Ser
                560                 565                 570

CTG CCC CAA CCG CCC AAG GAC GGA CCC ATC CTG GAG GTG GAG GAA GTG     1777
Leu Pro Gln Pro Pro Lys Asp Gly Pro Ile Leu Glu Val Glu Glu Val
575                 580                 585

GAG CTA CAG CCT GTT GTG GAG TCC CCT AAA GCC TCT GCC CCG ATT TAC     1825
Glu Leu Gln Pro Val Val Glu Ser Pro Lys Ala Ser Ala Pro Ile Tyr
590                 595                 600                 605

TCT GGG TAT GAG AAA CAC TTC CTG CCC ACA CCA GAG GAG CTG GGC CTT     1873
Ser Gly Tyr Glu Lys His Phe Leu Pro Thr Pro Glu Glu Leu Gly Leu
                610                 615                 620

CTA GTC TGATCTGCTT ACGGCTAGGG GCTGTACCCC TATCTTGGGC TAGACGTTTT      1929
Leu Val

TGTATTTTTA GATTTTTGAG ACAGGATCTC ACTATGGCTG ACCTGGAACT TGATATAACA   1989

ACCAGGCTGG CCTGGAACTC ACCAAGACTC ACCTGGTTTT GCCTTCCAAG GACTGAGAAG   2049

AAATGAGTGT GCCGCCTCCC GCCCAACCAG CTTTTGCTTT CCTTGCCTCT GGGTTCTTGG   2109

GCATCTGTTT GTTACTGCAG AAGAATCAGT GAGCTCACAG CCTCAACCCC ATCGTTGTTA   2169

TTTCCTCCTT GTGTCACAGG CTTGCTAGGT AGCCAAGGCT GGCCTCGAAC TTGTGATCCT   2229

CCCTGCTGCA GCATCCCCAG AGCTGGGATT ACAGGTGTGC GTCACTTCAT CGAGTCATAA   2289

CTTTTGATTC TAGTAAGAAT AACTACCAGG CAGGCTATGA AGGTGGTGAC TCGAAAGACA   2349

CATTCAAGGA CCTAAAGTGG TTAAGAGCCT GTGTTTTCTT GCAGTAGACC AAAGTTTGGT   2409

TCCCTGCCCT TGCAAAGGAC ACACGTTCAG TTTCCAGCAC CCACAGGGCA GCTCAGAATC   2469

ACCTGTAACT CCAGGTCCAA GGAATCCAAT GCCCTCTTCT GGCTTCTGTG AGCCCCGCAC   2529

ACACATGGTT ACTTATGCAC CGAAAAACAC ACGCATAAAA TAAAAATAAA TAATAAACC   2589
```

(2) INFORMATION FOR SEQ ID NO:7:

(i) SEQUENCE CHARACTERISTICS:

(A) LENGTH: 623 amino acids
(B) TYPE: amino acid
(D) TOPOLOGY: linear (ii) MOLECULE TYPE: protein (xi) SEQUENCE DESCRIPTION: SEQ ID NO:7:

```
Met Asn Arg Leu Arg Val Ala Arg Leu Thr Pro Leu Glu Leu Leu
 1               5                  10                  15

Ser Leu Met Ser Leu Leu Gly Thr Arg Pro His Gly Ser Pro Gly
                20                  25                  30

Pro Leu Gln Cys Tyr Ser Val Gly Pro Leu Gly Ile Leu Asn Cys Ser
                35                  40                  45

Trp Glu Pro Leu Gly Asp Leu Glu Thr Pro Val Leu Tyr His Gln
        50                  55                  60

Ser Gln Lys Tyr His Pro Asn Arg Val Trp Glu Val Lys Val Pro Ser
65                  70                  75                  80

Lys Gln Ser Trp Val Thr Ile Pro Arg Glu Gln Phe Thr Met Ala Asp
                85                  90                  95

Lys Leu Leu Ile Trp Gly Thr Gln Lys Gly Arg Pro Leu Trp Ser Ser
                100                 105                 110

Val Ser Val Asn Leu Glu Thr Gln Met Lys Pro Asp Thr Pro Gln Ile
                115                 120                 125

Phe Ser Gln Val Asp Ile Ser Glu Glu Ala Thr Leu Glu Ala Thr Val
                130                 135                 140

Gln Trp Ala Pro Pro Val Trp Pro Pro Gln Lys Ala Leu Thr Cys Gln
145                 150                 155                 160

Phe Arg Tyr Lys Glu Cys Gln Ala Glu Ala Trp Thr Arg Leu Glu Pro
                165                 170                 175

Gln Leu Lys Thr Asp Gly Leu Thr Pro Val Glu Met Gln Asn Leu Glu
                180                 185                 190

Pro Gly Thr Cys Tyr Gln Val Ser Gly Arg Cys Gln Val Glu Asn Gly
                195                 200                 205

Tyr Pro Trp Gly Glu Trp Ser Ser Pro Leu Ser Phe Gln Thr Pro Phe
        210                 215                 220

Leu Asp Pro Glu Asp Val Trp Val Ser Gly Thr Val Cys Glu Thr Ser
225                 230                 235                 240

Gly Lys Arg Ala Ala Leu Leu Val Trp Lys Asp Pro Arg Pro Cys Val
                245                 250                 255

Gln Val Thr Tyr Thr Val Trp Phe Gly Ala Gly Asp Ile Thr Thr Thr
                260                 265                 270

Gln Glu Glu Val Pro Cys Cys Lys Ser Pro Val Pro Ala Trp Met Glu
                275                 280                 285

Trp Ala Val Val Ser Pro Gly Asn Ser Thr Ser Trp Val Pro Pro Thr
        290                 295                 300

Asn Leu Ser Leu Val Cys Leu Ala Pro Glu Ser Ala Pro Cys Asp Val
305                 310                 315                 320

Gly Val Ser Ser Ala Asp Gly Ser Pro Gly Ile Lys Val Thr Trp Lys
                325                 330                 335

Gln Gly Thr Arg Lys Pro Leu Glu Tyr Val Val Asp Trp Ala Gln Asp
                340                 345                 350

Gly Asp Ser Leu Asp Lys Leu Asn Trp Thr Arg Leu Pro Pro Gly Asn
        355                 360                 365
```

```
Leu Ser Thr Leu Leu Pro Gly Glu Phe Lys Gly Val Pro Tyr Arg
    370                 375                 380

Ile Thr Val Thr Ala Val Tyr Ser Gly Gly Leu Ala Ala Pro Ser
385                 390                 395                 400

Val Trp Gly Phe Arg Glu Glu Leu Val Pro Leu Ala Gly Pro Ala Val
                405                 410                 415

Trp Arg Leu Pro Asp Asp Pro Pro Gly Thr Pro Val Val Ala Trp Gly
            420                 425                 430

Glu Val Pro Arg His Gln Leu Arg Gly Gln Ala Thr His Tyr Thr Phe
            435                 440                 445

Cys Ile Gln Ser Arg Gly Leu Ser Thr Val Cys Arg Asn Val Ser Ser
    450                 455                 460

Gln Thr Gln Thr Ala Thr Leu Pro Asn Leu His Ser Gly Ser Phe Lys
465                 470                 475                 480

Leu Trp Val Thr Val Ser Thr Val Ala Gly Gln Gly Pro Pro Gly Pro
                485                 490                 495

Asp Leu Ser Leu His Leu Pro Asp Asn Arg Ile Arg Trp Lys Ala Leu
            500                 505                 510

Pro Trp Phe Leu Ser Leu Trp Gly Leu Leu Leu Met Gly Cys Gly Leu
            515                 520                 525

Ser Leu Ala Ser Thr Arg Cys Leu Gln Ala Arg Cys Leu His Trp Arg
    530                 535                 540

His Lys Leu Leu Pro Gln Trp Ile Trp Glu Arg Val Pro Asp Pro Ala
545                 550                 555                 560

Asn Ser Asn Ser Gly Gln Pro Tyr Ile Lys Glu Val Ser Leu Pro Gln
                565                 570                 575

Pro Pro Lys Asp Gly Pro Ile Leu Glu Val Glu Val Glu Leu Gln
            580                 585                 590

Pro Val Val Glu Ser Pro Lys Ala Ser Ala Pro Ile Tyr Ser Gly Tyr
            595                 600                 605

Glu Lys His Phe Leu Pro Thr Pro Glu Glu Leu Gly Leu Leu Val
    610                 615                 620

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9670

(xi) SEQUENCE DESCRIPTION: SEQ ID NO:8:

ACCCCTGACC CCTGTTGAGA T                                      21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9671

(xi) SEQUENCE DESCRIPTION: SEQ ID NO:9:

GGTTCCCTGA TACCCACACA T                                      21
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (vii) IMMEDIATE SOURCE:
        (B) CLONE: AP1

(xi) SEQUENCE DESCRIPTION: SEQ ID NO:10:

CCATCCTAAT ACGACTCACT ATAGGGC                              27

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9673

(xi) SEQUENCE DESCRIPTION: SEQ ID NO:11:

GCCTTCTGCT CCAAAAGATG T                                    21

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: 9719

(xi) SEQUENCE DESCRIPTION: SEQ ID NO:12:

ACTCACTATA GGGCTCGAGC GGC                                23

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9672

(xi) SEQUENCE DESCRIPTION: SEQ ID NO:13:

GGGTCAGGGG TATGGTCTTC A                                    21

(2) INFORMATION FOR SEQ ID NO:14:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (vii) IMMEDIATE SOURCE:
        (B) CLONE: 6172

(xi) SEQUENCE DESCRIPTION: SEQ ID NO:14:

```
GTCGGTGCTC AGCATTCACT ACTCGAGGGT TTTTTTTTTT TTTTTTT                  47
```

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (vii) IMMEDIATE SOURCE:
        (B) CLONE: 9780

(xi) SEQUENCE DESCRIPTION: SEQ ID NO:15:

```
CGGAATTCGG CCATTCCTCG GGAACAGC                                      28
```

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: 9736

(xi) SEQUENCE DESCRIPTION: SEQ ID NO:16:

```
CCATACCCCT GACCCTGTT GAGAT                                          25
```

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: 9740

(xi) SEQUENCE DESCRIPTION: SEQ ID NO:17:

```
CAGAGGTTCC CTGATACCCA CACAT                                         25
```

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: 9826

(xi) SEQUENCE DESCRIPTION: SEQ ID NO:18:

```
GGCGACTTGA ACTGCTCGTG GGA                                           23
```

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: 9827

(xi) SEQUENCE DESCRIPTION: SEQ ID NO:19:

CGGCAGCGGC CATACACTTT GTA                                        23

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
            (vii) IMMEDIATE SOURCE:

(B) CLONE: 9559

(xi) SEQUENCE DESCRIPTION: SEQ ID NO:20:

HNTGGAGYGM NTGGAGY                                               17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: 9560

(xi) SEQUENCE DESCRIPTION: SEQ ID NO:21:

HNTGGAGYAR NTGGAGY                                               17

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9745

(xi) SEQUENCE DESCRIPTION: SEQ ID NO:22:

ATTCCCCGGG AACAGTTCAC C                                          21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: 9757

(xi) SEQUENCE DESCRIPTION: SEQ ID NO:23:

GACGGTCCCC GATACCCACA C                                          21

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: 9996

(xi) SEQUENCE DESCRIPTION: SEQ ID NO:24:

CTGAACTGCT CCTGGGAACC                                                    20

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (vii) IMMEDIATE SOURCE:
        (B) CLONE: 10002

(xi) SEQUENCE DESCRIPTION: SEQ ID NO:25:

AGGAGTCAGC CCATCTGTCT TC                                                 22

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Gly Gly Ser Gly
1

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (vii) IMMEDIATE SOURCE:
        (B) CLONE: 10302

(xi) SEQUENCE DESCRIPTION: SEQ ID NO:27:

AACCTCAGCA CATTGTTACC AGGG                                               24

(2) INFORMATION FOR SEQ ID NO:28:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (vii) IMMEDIATE SOURCE:
        (B) CLONE: 10305

(xi) SEQUENCE DESCRIPTION: SEQ ID NO:28:

CCGCTCGAGT CCGCTTCCTC CCCTGATCCT ATTATCTGGT AG                           42

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
    (vii) IMMEDIATE SOURCE:
          (B) CLONE: 10381

(xi) SEQUENCE DESCRIPTION: SEQ ID NO:29:

CCACTACACC TTGTGTGC                                                      18

(2) INFORMATION FOR SEQ ID NO:30:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (vii) IMMEDIATE SOURCE:
          (B) CLONE: 10390

(xi) SEQUENCE DESCRIPTION: SEQ ID NO:30:

TAGTAGCAGA TCTGGGCTCC CTCAGGGTGT TATCTGG                                  37

(2) INFORMATION FOR SEQ ID NO:31:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (vii) IMMEDIATE SOURCE:
          (B) CLONE: 10314

(xi) SEQUENCE DESCRIPTION: SEQ ID NO:31:

TCGTGATTCT CTGGTCGGTG                                                    20

(2) INFORMATION FOR SEQ ID NO:32:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (vii) IMMEDIATE SOURCE:
          (B) CLONE: 10315

(xi) SEQUENCE DESCRIPTION: SEQ ID NO:32:

GTGATTGCTT TGGCGGTGAG                                                    20

(2) INFORMATION FOR SEQ ID NO:33:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (vii) IMMEDIATE SOURCE:
          (B) CLONE: 10382

(xi) SEQUENCE DESCRIPTION: SEQ ID NO:33:

GAGTTCAAAG GAGGGGTAC                                                     19

(2) INFORMATION FOR SEQ ID NO:34:

(i) SEQUENCE CHARACTERISTICS:
          (A) LENGTH: 40 base pairs
          (B) TYPE: nucleic acid
          (C) STRANDEDNESS: single
          (D) TOPOLOGY: linear
```

```
        (vii) IMMEDIATE SOURCE:
              (B) CLONE: 10388

(xi) SEQUENCE DESCRIPTION: SEQ ID NO:34:

TAGTAGCAGA TCTGGGCTCC CTGATCCTAT TATCTGGTAG                             40

(2) INFORMATION FOR SEQ ID NO:35:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (vii) IMMEDIATE SOURCE:
              (B) CLONE: 10123

(xi) SEQUENCE DESCRIPTION: SEQ ID NO:35:

CCGTACGGAT CCGCCGGGCC ACTGCAGTGC TAC                                   33

(2) INFORMATION FOR SEQ ID NO:36:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (vii) IMMEDIATE SOURCE:
              (B) CLONE: 10116

(xi) SEQUENCE DESCRIPTION: SEQ ID NO:36:

GTACAGAATT CAATCTTTTG GAGCAGAAGG CGGTGT                                36

(2) INFORMATION FOR SEQ ID NO:37:

(i) SEQUENCE CHARACTERISTICS:
              (A) LENGTH: 31 base pairs
              (B) TYPE: nucleic acid
              (C) STRANDEDNESS: single
              (D) TOPOLOGY: linear (vii) IMMEDIATE SOURCE:
              (B) CLONE: 10124

(xi) SEQUENCE DESCRIPTION: SEQ ID NO:37:

TGGGTGCTTT TCCAGCGGAC GCGTCCCCAG G                                     31

(2) INFORMATION FOR SEQ ID NO:38:

(i) SEQUENCE CHARACTERISTICS:
              (A) LENGTH: 35 base pairs
              (B) TYPE: nucleic acid
              (C) STRANDEDNESS: single
              (D) TOPOLOGY: linear (vii) IMMEDIATE SOURCE:
              (B) CLONE: 10122

(xi) SEQUENCE DESCRIPTION: SEQ ID NO:38:

GATCCCTGGG GACGCGTCCG CTGGAAAAGC ACCCA                                 35

(2) INFORMATION FOR SEQ ID NO:39:

(i) SEQUENCE CHARACTERISTICS:
              (A) LENGTH: 36 base pairs
              (B) TYPE: nucleic acid
              (C) STRANDEDNESS: single
```

```
            (D) TOPOLOGY: linear (vii) IMMEDIATE SOURCE:
          (B) CLONE: 10182

(xi) SEQUENCE DESCRIPTION: SEQ ID NO:39:

GGAAAGGGAT CCCCAGGCCC ACTGCAGTGC TACAGC                                    36

(2) INFORMATION FOR SEQ ID NO:40:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (vii) IMMEDIATE SOURCE:
          (B) CLONE: 10200

(xi) SEQUENCE DESCRIPTION: SEQ ID NO:40:

GTCGTCCTCG AGCTAATCTT CAGGATCTAA GAATGGCGTC                                40

(2) INFORMATION FOR SEQ ID NO:41:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (vii) IMMEDIATE SOURCE:
          (A) LIBRARY: 10184

(xi) SEQUENCE DESCRIPTION: SEQ ID NO:41:

ATGTCGCTGC TGCTCGGGAC GCGGCCCCAC G                                         31

(2) INFORMATION FOR SEQ ID NO:42:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (vii) IMMEDIATE SOURCE:
          (B) CLONE: 10183

(xi) SEQUENCE DESCRIPTION: SEQ ID NO:42:

GATCCGTGGG GCCGCGTCCC GAGCAGCAGC GACAT                                     35
```

HEMATOPOIETIC CYTOKINE RECEPTOR

CROSS-REFERENCE TO RELATED APPLICATIONS

This application is continuation of application Ser. No. 09/073,594, filed May 6, 1998, now U.S. Pat. No. 5,925,735 which is a divisional of application Ser. No. 08/653,740, filed May 23, 1996, now U.S. Pat. No. 5,792,850.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signalling pathways within the cell, such as second messenger systems. Other classes of receptors are soluble molecules, such as the transcription factors.

Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia or receiving chemotherapy for cancer. The demonstrated in vivo activities of these cytokines illustrates the enormous clinical potential of, and need for, other cytokines, cytokine agonists, and cytokine antagonists.

The present invention addresses these needs by providing new hematopoietic cytokine receptors, as well as related compositions and methods.

SUMMARY OF THE INVENTION

The present invention provides novel receptor polypeptides, polynucleotides encoding the polypeptides, and related compositions and methods.

Within one aspect there is provided an isolated polynucleotide encoding a ligand-binding receptor polypeptide comprising a sequence of amino acids selected from the group consisting of (a) residues 33 to 235 of SEQ ID NO:3, (b) allelic variants of (a), and (c) sequences that are at least 60% identical to (a) or (b). Within one embodiment, the polypeptide further comprises a fibronectin type III domain. Within a related embodiment, the polypeptide comprises residues 33 to 514 of SEQ ID NO:3, residues 25 to 508 of SEQ ID NO:7, or an allelic variant of one of these sequences. Within another embodiment, the polypeptide further comprises a transmembrane domain, such as residues 515 to 540 of SEQ ID NO:3, residues 509 to 533 of SEQ ID NO:7, or an allelic variant of one of these sequences. The polypeptide may further comprise an intracellular domain. Preferred intracellular domains include residues 541 to 578 of SEQ ID NO:3, residues 541 to 636 or SEQ ID NO:5, residues 534 to 623 of SEQ ID NO:7, and allelic variants of these sequences. Within additional embodiments, the polypeptide comprises (a) residues 33 to 578 of SEQ ID NO:3, (b) residues 33 to 636 of SEQ ID NO:5, (c) residues 25 to 623 of SEQ ID NO:7 or (d) an allelic variant of (a), (b), or (c). Within additional embodiments, the isolated polynucleotide is a DNA comprising a sequence of nucleotides as shown in SEQ ID NO:2 from nucleotide 23 to nucleotide 1756, SEQ ID NO:4 from nucleotide 139 to nucleotide 2046, or SEQ ID NO:6 from nucleotide 11 to nucleotide 1879.

The polypeptides encoded by the isolated polynucleotides disclosed above may further comprise an affinity tag. Within certain embodiments of the invention, the affinity tag is polyhistidine, protein A, glutathione S transferase, substance P, maltose binding protein, or an immunoglobulin heavy chain constant region.

Within a second aspect of the invention there is provided an expression vector comprising a transcription promoter, a DNA segment encoding a secretory peptide and a ligand-binding receptor polypeptide as disclosed above, and a transcription terminator, wherein the promoter, DNA segment, and terminator are operably linked. Within one embodiment, the ligand-binding receptor polypeptide is a chimeric polypeptide, wherein the chimeric polypeptide consists essentially of a first portion and a second portion joined by a peptide bond. The first portion of the chimeric polypeptide is a ligand binding domain of a receptor polypeptide selected from the group consisting of (a) a receptor polypeptide as shown in SEQ ID NO:3, (b) allelic variants of (a), and (c) receptor polypeptides that are at least 60% identical to (a) or (b), and is substantially free of transmembrane and intracellular polypeptide segments; and the second portion consists essentially of an affinity tag as disclosed above.

Within a third aspect of the invention there is provided a cultured cell into which has been introduced an expression vector as disclosed above, wherein the cell expresses a receptor polypeptide encoded by the DNA segment. Within one embodiment of the invention the cell further expresses gp130 or leukemia inhibitory factor (LIF) receptor. Within another embodiment of the invention the cell is dependent upon an exogenously supplied hematopoietic growth factor for proliferation.

Within a fourth aspect, the present invention provides an isolated polypeptide comprising a segment selected from the group consisting of (a) residues 33 to 235 of SEQ ID NO:3, (b) allelic variants of (a), and (c) sequences that are at least 60% identical to (a) or (b), wherein the polypeptide is substantially free of transmembrane and intracellular domains ordinarily associated with hematopoietic receptors. Within one embodiment, the polypeptide further comprises an affinity tag, such as polyhistidine, protein A, glutathione S transferase, substance P, maltose binding protein, or an immunoglobulin Fc polypeptide. Within another embodiment, the polypeptide is immobilized on a solid support. Within a further embodiment, the polypeptide is a chimeric polypeptide consisting essentially of a first portion and a second portion joined by a peptide bond, the first portion consisting essentially of a ligand binding domain of a receptor polypeptide selected from the group consisting of (a) a receptor polypeptide as shown in SEQ ID NO:3, (b) allelic variants of (a), and (c) receptor polypeptides that are at least 60% identical to (a) or (b), and the second portion consisting essentially of an affinity tag.

Within a fourth aspect of the invention there is provided a method for detecting a ligand within a test sample, comprising contacting a test sample with a polypeptide as disclosed above and detecting binding of the polypeptide to ligand in the sample. Within one embodiment, the polypeptide is membrane-bound within a cultured cell, and the detecting step comprises measuring a biological response in the cultured cell. Within a related embodiment the biological response is cell proliferation or activation of transcription of a reporter gene. Within an alternative embodiment, the polypeptide is immobilized on a solid support.

The invention further provides an antibody that specifically binds to a polypeptide as disclosed above.

These and other aspects of the invention will become evident upon reference to the following detailed description and the attached drawing.

BRIEF DESCRIPTION OF THE DRAWING

The FIGURE illustrates conserved structural features in cytokine receptors.

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. Cell-surface cytokine receptors are characterized by a multi-domain structure as discussed in more detail below. These receptors are anchored in the cell membrane by a transmembrane domain characterized by a sequence of hydrophobic amino acid residues (typically about 21–25 residues), which is commonly flanked by positively charged residues (Lys or Arg). The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Receptor polypeptides are said to be substantially free of transmembrane and intracellular polypeptide segments when they lack sufficient portions of these segments to provide membrane anchoring or signal transduction, respectively.

The present invention is based in part upon the discovery of a novel DNA sequence that encodes a protein having the structure of a cytokine receptor, including the conserved WSXWS motif (SEQ ID NO:1). An isolated human cDNA encoding this receptor (a representative sequence of which is shown in SEQ ID NO:2) included an open reading frame encoding 578 amino acids. The deduced amino acid sequence indicated that the encoded receptor belonged to the receptor subfamily that includes the G-CSF, IL-6, CNTF, IL-11, OSM, LIF, CT-1, and gp130 receptors. In addition to the WSXWS motif at residues 217–221 of SEQ ID NO:3, the receptor comprises a cytokine-binding region of approximately 200 amino acid residues (residues 33 to 235 of SEQ ID NO:3), three fibronectin type III domains (residues 236 to 514 of SEQ ID NO:3), a transmembrane domain (residues 515 to 540 of SEQ ID NO:3), and an intracellular or signalling domain (residues 541 to 578of SEQ ID NO:3). Those skilled in the art will recognize that these domain boundaries are approximate and are based on alignments with known proteins and predictions of protein folding. In addition to these domains, conserved receptor features in the encoded receptor include (with reference to SEQ ID NO:3) a conserved Cys-X-Trp domain at residues 52–54, a Cys residue at position 41, a Trp residue at position 151, and an Arg residue at position 207. This receptor has been designated "Zcytor1".

Those skilled in the art will recognize that the sequences shown in SEQ ID NO:2 and SEQ ID NO:3 represent a single allele of the human receptor gene, and that allelic variation and alternative splicing are expected to occur. A second, apparently alternatively spliced, human cDNA was also isolated, which encoded a protein with a 58 amino acid residue insertion near the carboxyl terminus relative to SEQ ID NO:3. The nucleotide sequence and deduced amino acid sequence of this longer clone are shown in SEQ ID NO:4 and SEQ ID NO:5. Allelic variants can be cloned by probing cDNA or genomic libraries from different individuals according to standard procedures.

The present invention further provides counterpart receptors and polynucleotides from other species ("species orthologs"). Of particular interest are ZCytor1 receptors from other mammalian species, including murine, porcine, ovine, bovine, canine, feline, equine, and non-human primate receptors. Species orthologs of the human ZCytor1 receptor can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones. The DNA and deduced amino acid sequences of a representative mouse Zcytor1 clone are shown in SEQ ID NO:6 and SEQ ID NO:7, respectively.

The approximate domain boundaries (amino acid residues) of the human (SEQ ID NO:3 and NO:5 ) and mouse (SEQ ID NO:7) Zcytor1 receptors are shown in Table 1.

TABLE 1

| Domain | Human | Mouse |
|---|---|---|
| Ligand-binding | 33–514 | 25–508 |
| Hematopoietin | 33–235 | 25–229 |
| Fibronectin Type III | 236–514 | 230–508 |
| Transmembrane | 515–540 | 509–533 |
| Intracellular | 541–578 (SEQ ID NO: 3) 541–636 (SEQ ID NO: 5) | 534–623 |

Analysis of the tissue distribution of the mRNA corresponding to this novel DNA showed that expression was widespread, with high levels of expression observed in lymphoid tissues, including thymus, spleen, lymph nodes, and peripheral blood leukocytes. The receptor is present on both B- and T-cells, with T-cell levels generally higher. These data indicate a role for the Zcytor1 receptor in proliferation, differentiation, and/or activation of immune cells, and suggest a role in development and regulation of immune responses. The data also suggest that the interaction of Zcytor1 with its ligand may stimulate proliferation and development of myeloid cells and may, like IL-6, LIF, IL-11 and OSM (Baumann et al., *J. Biol. Chem.* 2:8414–8417, 1993), induce acute-phase protein synthesis in hepatocytes.

Cytokine receptor subunits are characterized by a multi-domain structure comprising an extracellular domain, a transmembrane domain that anchors the polypeptide in the cell membrane, and an intracellular domain. The extracellular domain may be a ligand-binding domain, and the intracellular domain may be an effector domain that is involved in signal transduction, although ligand-binding and effector functions may reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of the structure (as shown in the attached FIGURE) and function. Hematopoietic receptors, for example, are characterized by the presence of a domain containing conserved cysteine residues and the WSXWS motif (SEQ ID NO:1). Additional domains, including protein kinase domains; fibronectin type III domains; immunoglobulin domains, which are characterized by disulfide-bonded loops; and TNF domains, are present in certain hematopoietic receptors. Cytokine receptor structure has been reviewed by Urdal, *Ann. Reports Med. Chem.* 26:221–228, 1991 and Cosman, *Cytokine* 5:95–106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members. The cytokine receptor superfamily is subdivided as shown in Table 2.

TABLE 2

Cytokine Receptor Superfamily

Immunoglobulin family

CSF-1 receptor
MGF receptor
IL-1 receptor
PDGF receptor
Hematopoietin family erythropoietin receptor
G-CSF receptor
IL-2 receptor b-subunit
IL-3 receptor
IL-4 receptor
IL-5 receptor
IL-6 receptor
IL-7 receptor
IL-9 receptor
GM-CSF receptor a-subunit
GM-CSF receptor b-subunit
Prolactin receptor
CNTF receptor
Oncostatin M receptor
Leukemia inhibitory factor receptor

TABLE 2-continued

Cytokine Receptor Superfamily

TNF receptor

TNF (p80) receptor
TNF (p60) receptor
TNFR-RP
CD27
CD30
CD40
4-1BB
OX-40
Fas
NGF receptor
Other IL-2 receptor α-subunit
IL-15 receptor α-subunit
IFN-γ receptor Analysis of the Zcytor1 sequence suggests that it is a member of the same receptor subfamily as the IL-6, IL-11, G-CSF, CNTF, OSM, CT-1, and leukemia inhibitory factor (LIF) receptors. Certain receptors in this subfamily (e.g., G-CSF) associate to form homodimers that transduce a signal. Other members of the subfamily (e.g., IL-6, IL-11, and LIF receptors) combine with a second subunit (termed β-subunit) to bind ligand and transduce a signal. Specific β-subunits associate with a plurality of specific cytokine receptor subunits. For example, the β-subunit gp130 (Hibi et al., *Cell* 63:1149–1157, 1990) associates with receptor subunits specific for IL-6, IL-11, and LIF (Gearing et al., *EMBO J.* 10:2839–2848, 1991; Gearing et al., U.S. Pat. No. 5,284, 755). Oncostatin M binds to a heterodimer of LIF receptor and gp130. CNTF binds to trimeric receptors comprising CNTF receptor, LIF receptor, and gp130 subunits. The longer form of human Zcytor1 shown in SEQ ID NO:5 comprises an extended intracellular domain.

Within preferred embodiments of the invention the isolated polynucleotides will hybridize to similar sized regions of SEQ ID NO:2, SEQ ID NO:4, or SEQ ID NO:6, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from spleen or thymus, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl Acad. Sci. USA* 69:1408–1412, 1972). Complementary DNA (cDNA) is prepared from poly(A)$^+$ RNA using known methods. Polynucleotides encoding Zcytor1 polypeptides are then identified and isolated by, for example, hybridization or PCR.

The present invention also provides isolated receptor polypeptides that are substantially homologous to the receptor polypeptides of SEQ ID NO:3, NO:5, NO:7, and their species orthologs. By "isolated" is meant a protein or polypeptide which is found in a condition other than its native environment, such as apart from blood and animal tissue. In a preferred form, the isolated polypeptide is substantially free of other polypeptides, particularly other polypeptides of animal origin. It is prefered to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO:3, NO:5, NO:7, or their species orthologs. Such polypeptides will more preferably be at least 90% identical, and most preferably 95% or more identical to SEQ ID NO:3, NO:5, NO:7, or their species orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 8:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | 4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |

TABLE 3-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins are characterized as having one or more amino acid substitutions, deletions or additions. These changes are preferably of a minor nature, that is conservative amino acid substitutions (see Table 4) and other substitutions that do not significantly affect the folding or activity of the protein; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 6:31, 1988), maltose binding protein (Kellerman and Ferenci, *Methods Enzymol.* 90:459–463, 1982; Guan et al., *Gene* 67:21–30, 1987), or other antigenic epitope or binding domain. See, in general Ford et al., *Protein Expression and Purification* 2:95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the polypeptides of the present invention can be identified according to procedures known in the art, such as site-directed mutagenesis or alanine-scanning mutagenesis (Cunningham and Wells, *Science* 2, 1081–1085, 1989). In the latter technique, single alanine mutations are introduced at every residue in the molecule, and the resultant mutant molecules are tested for biological activity (e.g. ligand binding and signal transduction) to identify amino acid residues that are critical to the activity of the molecule. See also, Hilton et al., *J. Biol. Chem.* 2:4699–4708, 1996. Sites of ligand-receptor interaction can also be determined by analysis of crystal structure as determined by such techniques as nuclear magnetic resonance, crystallography or photoaffinity labeling. See, for example, de Vos et al., *Science* 255:306–312, 1992; Smith et al., *J. Mol. Biol.* 224:899–904, 1992; Wlodaver et al., *FEBS Left.* 309:59–64, 1992. The identities of essential amino acids can also be inferred from analysis of homologies with related receptors.

Multiple amino acid substitutions can be made and tested using known, methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lauman et al., *Biochemist* 3:10832–10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 33 to 235 of SEQ ID NO:3 or allelic variants or species orthologs thereof and retain ligand-binding activity. Such polypeptides may include additional amino acids from an extracellular ligand-binding domain (e.g, one or more fibronectin type III domains) of a Zcytor1 receptor as well as part or all of the transmembrane and intracellular domains. Such polypeptides may also include additional polypeptide segments as generally disclosed above.

The receptor polypeptides of the present invention, including full-length receptors, receptor fragments (e.g., ligand-binding fragments), and fusion proteins can be produced in genetically engineered host cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a receptor polypeptide of the present invention is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a receptor polypeptide of the present invention into the secretory pathway of a host cell, a secretory signal sequence (also known as a leader sequence, prepro sequence or pre sequence) is provided in the expression vector. The secretory signal sequence may be that of the receptor, or may be derived from another secreted protein (e.g., t-PA) or synthesized de novo. The secretory signal sequence is joined to the DNA sequence encoding a protein of the present invention in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., N.Y., 1987), and liposome-mediated transfection (Hawley-Nelson et al., *Focus* 15:73, 1993; Ciccarone et al., *Focus* 15:80, 1993) which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign proteins therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (Bangaloro 11:47–58, 1987.

Fungal cells, including yeast cells, and particularly cells of the genus Saccharomyces, can also be used within the present invention, such as for producing receptor fragments or polypeptide fusions. Methods for transforming yeast cells with exogenous DNA and producing recombinant proteins therefrom are disclosed by, for is example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Within one aspect of the present invention, a cytokine receptor (including transmembrane and intracellular domains) is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing the novel receptors of the present invention and transducing a receptor-mediated signal include cells that express a β-subunit, such as gp130, and cells that co-express gp130 and LIF receptor (Gearing et al., *EMBO J.* 10:2839–2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include the human TF-1 cell line (ATCC number CRL-2003) and the DA-1 cell line (Branch et al., *Blood* 62:1782, 1987; Broudy et al., *Blood* 75:1622–1626, 1990). In the alternative, suitable host cells can be engineered to produce a β-subunit or other cellular component needed for the desired cellular response. For example, the murine cell line BaF3 (Palacios and Steinmetz, *Cell* 41:727–734, 1985; Mathey-Prevot et al., *Mol, Cell. Biol.* 6: 4133–4135, 1986), a baby hamster kidney (BHK) cell line, or the CTLL-2 cell line (ATCC TIB-214) can be transfected to express the mouse gp130 subunit, or mouse gp130 and LIF receptor, in addition to Zcytor1. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a Zcytor1 ligand. Cells expressing functional Zcytor1 are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE (see, for example, Shaw et al., *Cell* 5:563–572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094–29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell- or tissue-conditioned media samples can be assayed on a target cell to identify cells that produce ligand. Positive cells are then used to produce a cDNA library in a mammalian cell expression vector, which is divided into pools, transfected into host cells, and expressed. Media samples from the transfected cells are then assayed, with subsequent division of pools, retransfection, subculturing, and re-assay of positive cells to isolate a clonal cell line expressing the ligand. Media samples conditioned by kidney, liver, spleen, thymus, other lymphoid tissues, or T-cells are preferred sources of ligand for use in screening procedures.

A natural ligand for Zcytor1 can also be identified by mutagenizing a cytokine-dependent cell line expressing Zcytor1 and culturing it under conditions that select for autocrine growth. See WIPO publication WO 95/21930. Within a typical procedure, cells expressing Zcytor1 are mutagenized, such as with EMS. The cells are then allowed to recover in the presence of the required cytokine, then transferred to a culture medium lacking the cytokine. Surviving cells are screened for the production of a ligand for Zcytor1, such as by adding soluble (ligand-binding) receptor polypeptide to the culture medium or by assaying conditioned media on wild-type cells and transfected cells expressing the Zcytor1. Preferred cell lines for use within this method include cells that are transfected to express gp130 or gp130 in combination with LIF receptor. Preferred such host cell lines include transfected CTLL-2 cells (Gillis and Smith, *Nature* 268:154–156, 1977) and transfected BaF3 cells.

Additional assays provided by the present invention include the use of hybrid receptor polypeptides. These hybrid polypeptides fall into two general classes. Within the first class, the intracellular domain of Z-Cytor1, comprising approximately residues 5541 to 636 of SEQ ID NO:5, is joined to the ligand-binding domain of a second receptor. It is preferred that the second receptor be a hematopoietic cytokine receptor, such as mp1 receptor (Souyri et al., *Cell* 63:1137–1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by Z-Cytor1 while using readily available ligands. This system can also be used to determine if particular cell lines are capable of responding to signals transduced by Z-Cytor1. A second class of hybrid receptor polypeptides comprise the extracellular (ligand-binding) domain of ZCytor1 (approximately residues 33 to 514 of SEQ ID NO:3) with a cytoplasmic domain of a second receptor, preferably a hematopoietic cytokine receptor, and a transmembrane domain. Hybrid receptors of this second class are expressed in cells known to be capable of responding to signals transduced by the second receptor. Together, these two classes of hybrid receptors enable the use of a broad spectrum of cell types within receptor-based assay systems.

Cells found to express a ligand for Zcytor1 are then used to prepare a cDNA library from which the ligand-encoding cDNA may be isolated as disclosed above. The present invention thus provides, in addition to novel receptor polypeptides, methods for cloning polypeptide ligands for the receptors.

The tissue specificity of Zcytor1 expression suggests a role in early thymocyte development and immune response regulation. These processes involve stimulation of cell proliferation and differentiation in response to the binding of one or more cytokines to their cognate receptors. In view of the tissue distribution observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages in culture.

Agonist ligands for Zcytor1 may be useful in stimulating cell-mediated immunity and for stimulating lymphocyte proliferation, such as in the treatment of infections involving immunosuppression, including certain viral infections. Additional uses include tumor suppression, where malignant transformation results in tumor cells that are antigenic. Agonist ligands could be used to induce cytotoxicity, which may be mediated through activation of effector cells such as T-cells, NK (natural killer) cells, or LAK (lymphoid activated killer) cells. Agonist ligands may also be useful in treating leukopenias by increasing the levels of the affected cell type, and for enhancing the regeneration of the T-cell repertoire after bone marrow transplantation.

Antagonist ligands may find utility in the suppression of the immune system, such as in the treatment of autoimmune diseases, including rheumatoid arthritis, multiple sclerosis, diabetes mellitis, etc. Immune suppression can also be used to reduce rejection of tissue or organ transplants and grafts and to treat T-cell specific leukemias of lymphomas by inhibiting proliferation of the affected cell type.

Zcytor1 may also be used within diagnostic systems for the detection of circulating levels of ligand. Within a related embodiment, antibodies or other agents that specifically bind to Zcytor1 can be used to detect circulating receptor polypeptides. Elevated or depressed levels of ligand or receptor polypeptides may be indicative of pathological conditions, including cancer. Soluble receptor polypeptides may contribute to pathologic processes and can be an indirect marker of an underlying disease. For example, elevated levels of soluble IL-2 receptor in human serum have been associated with a wide variety of inflammatory and neoplastic conditions, such as myocardial infarction, asthma, myasthenia gravis, rheumatoid arthritis, acute T-cell leukemia, chronic lymphocytic leukemia, colon cancer, breast cancer, and ovarian cancer (Heaney et al., *Blood* 87:847–857, 1996).

A ligand-binding poypeptide of a ZCytor1 receptor can be prepared by expressing a truncated DNA encoding residues 33 through 235 of the human receptor (SEQ ID NO:3) or the corresponding region of a non-human receptor. Additional residues of the receptor may also be included, in particular carboxyl-terminal residues from residue 236 up to and including residue 514 of SEQ ID NO:3. It is preferred that the extracellular domain be prepared in a form substantially free of transmembrane and intracellular polypeptide segments. To direct the export of a receptor polypeptide from the host cell, the receptor DNA is linked to a second DNA segment encoding a secretory peptide, such as a t-PA secretory peptide or a Zcytor1 secretory peptide. To facilitate purification of the secreted receptor polypeptide, a C-terminal extension, such as a poly-histidine tag, substance P, Flag™ peptide (Hopp et al., *Bio/Technology* 6:1204–1210, 1988; available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_C$ fragment, which contains two constant region domains and lacks the variable region. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a Zcytor1-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Collected fractions can be re-fractionated until the desired level of purity is reached. The receptor-Ig chimeras can also be used within assay systems to specifically bind and neutralize Zcytor1 ligand. For use in assays, the chimeras are bound to a support via the $F_C$ region and used in an ELISA format.

A preferred assay system employing a ligand-binding receptor fragment uses a commercially available biosensor instrument (BIAcore™, Pharmacia Biosensor, Piscataway, N.J.), wherein the receptor polypeptide is immobilized onto the surface of a receptor chip. Use of this instrument is disclosed by Karlsson, *J. Immunol. Methods* 145:229–240, 1991 and Cunningham and Wells, *J. Mol. Biol.* 234:554–563, 1993. A receptor polypeptide can be covalently attached, using amine or sulfhydryl chemistry, directly to dextran fibers that are attached to gold film within the flow cell. In the alternative, the receptor polypeptide can be coupled to the chip via an antibody. Within one embodiment, a receptor polypeptide comprising a ligand-binding domain fused to an immunoglobulin $F_c$ fragment is coupled via a second (anti-IgG) antibody that is bound to the chip. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see, Scatchard, *Ann. N.Y. Acad. Sci.* 51: 660–672, 1949) and calorimetric assays (Cunningham et al., *Science* 253:545–548, 1991; Cunningham et al., *Science* 245:821–825, 1991).

A Zcytor1 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

Zcytor1 polypeptides can also be used to prepare antibodies that specifically bind to Zcytor1 polypeptides. Polypeptides useful in this regard include fusion polypeptides, such as fusions of Zcytor1 or a portion thereof with an immunoglobulin polypeptide or maltose binding protein. As used herein, the term "antibodies" includes polyclonal antibodies, monoclonal antibodies, antigen-binding fragments thereof such as F(ab')$_2$ and Fab fragments, and the like, including genetically engineered antibodies. Antibodies are defined to be specifically binding if they bind to a Zcytor1 polypeptide with a $K_a$ at least 2 logs greater than the $K_a$ of binding to other proteins. The affinity of a monoclonal antibody can be readily determined by one of ordinary skill in the art (see, for example, Scatchard, ibid.).

Methods for preparing polyclonal and monoclonal antibodies are well known in the art (see for example, Sambrook et al., *Molecular Cloning: A Laboratory Manual,* 2nd edition, Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies may be generated from a variety of warm-blooded animals such as horses, cows, goats, sheep, dogs, chickens, rabbits, mice, and rats. The immunogenicity of a Zcytor1 polypeptide may be increased through the use of an adjuvant such as Freund's complete or incomplete adjuvant. A variety of assays known to those skilled in the art can be utilized to detect antibodies which specifically bind to Zcytor1 polypeptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blotting (Towbin, *Proc. Natl. Acad. Sci. USA* 76:4350, 1979) inhibition or competition assays, and sandwich assays.

Antibodies to Zcytor1 are useful for tagging cells that express the receptor and assaying Zcytor1 expression levels, for affinity purification, within diagnostic assays for determining circulating levels of soluble receptor polypeptides, analytical methods employing fluorescence-activated cell sorting. Divalent antibodies may be used as agonists to mimic the effect of the Zcytor1 ligand.

The invention is further illustrated by the following non-limiting examples.

EXAMPLE 1

A cDNA library was prepared from human placental poly A$^+$ RNA provided as a control in a Marathon™ cDNA Amplification Kit (Clontech Laboratories, Inc., Palo Alto, Calif.) using the protocol provided by the manufacturer. This cDNA was used as template in polymerase chain reactions.

Primers were designed from the sequence of an expressed sequence tag (EST) that was identified by homology to human gp130. The primers were used to amplify a cDNA corresponding to the EST from the placenta library using the polymerase chain reaction (PCR). PCR was performed using 5 μL of a 1:50 dilution of the human placenta cDNA as template, 5 μl 10× PCR buffer (Boehringer Mannheim, Indianapolis, Ind.), 5 μl 10× dNTPs (Perkin Elmer, Norwalk, Conn.), 0.5 μl (2.5 units) Taq polymerase (Boehringer Mannheim), 50 pmoles each of oligonucleotide primers 9670 (SEQ ID NO:8) and 9671 (SEQ ID NO:9) in a reaction volume of 50 μl. The mixture was incubated at 95° C. for one minute, followed by 25 cycles of 55° C., 20 seconds; 72° C., one minute; 95° C., 15 seconds. The mixture was then incubated at 72° C. for 7 minutes.

The DNA resulting from the first PCR was then re-amplified using the same primers. One μl of template DNA was combined with 50 pmoles of each primer, 5 μl 10× PCR buffer (Boehringer Mannheim), 5 μl 2 mM dNTPs (Perkin-Elmer), 0.5 μl (2.5 units) Taq polymerase (Boehringer Mannheim) in a reaction volume of 50 μl. The reaction was run for 30 cycles of 94° C. for one minute, 60° C. for one minute, then 72° C. for 2.5 minutes; then incubated at 72° C. for 7 minutes. The amplified product, designated 13—13, was purified by electrophoresis on a agarose gel and purified.

EXAMPLE 2

Receptor DNA was also prepared by PCR from Marathon™ Ready cDNA (Clontech Laboratories). Five μl of fetal brain cDNA was amplified by PCR (3' RACE reaction) in a 50 μl reaction mixture containing 50 pmoles primer 9670 (SEQ ID NO:8), 5 μl 10× dNTPs (Perkin-Elmer Corporation), 5 μl Takara 10× buffer (PanVera Corp., Madison, Wis.), 1 μl 1:1 ExTaq polymerase (Takara., Otsu, Shiga, Japan)/TaqStart™ antibody (Clontech Laboratories, Inc.). The mixture was incubated at 95° C. for one minute, then cycled 10 times at 60° C., 30 seconds; 72° C., 2 minutes; 95° C., 30 seconds, then held at 60° C. 10 μmole primer API (SEQ ID NO:10; obtained from Clontech Laboratories) was added, and the reaction was continued for another 25 cycles followed by a 7 minute incubation at 72° C. A 5' RACE reaction was carried out in the same manner, except primer 9671 (SEQ ID NO:9) was used.

The 5' and 3' reaction products were then amplified using nested primers. 5 μl of the 3' RACE reaction mixture was amplified using 50 pMoles of primer 9673 (SEQ ID NO:11), 50 pMoles primer 9719 (SEQ ID NO:12), 5 μl 10× dNTPs (Takara Shuzo Co., Ltd), 5 μl Takara 10× buffer, 1 μl 1:1 ExTaq/Taqstart antibody in a 50 μl reaction mixture. The mixture was incubated at 95° C. for one minute; then run for 30 cycles at 60° C., 30 seconds; 72° C., 2 minutes; 95° C., 30 seconds; followed by a 7 minute incubation at 72° C. A similar reaction was run using 5 µl of the 5' race reaction products as template and oligonucleotide primers 9672 (SEQ ID NO:13) and 9719 (SEQ ID NO:12).

A 3' reaction product of approximately 1750 bp and a 5' reaction product of approximately 600 bp were isolated from the PCR reaction mixtures by electrophoresis on low-melt agarose gels. The fragments were ligated into the vector pGEM®-T (Promega Corp., Madison, WI). Subcloned fragments were sequenced. A representative human Zcytor1 DNA sequence is shown in SEQ ID NO:2. This sequence was generated from data obtained from subclones #9 (5' RACE product), #28 (3' RACE product), fragment 13—13 (Example 1), and the original EST.

EXAMPLE 3

Total RNA was prepared from ~2.7×10$^8$ K-562 cells (ATCC CCL 243) using guanidine isothiocyanate followed by CsCl centrifugation (Chirgwin et al., ibid.). Poly(A)$^+$ RNA was isolated using an OLIGOTEX-dT-mRNA isolation kit (Qiagen Inc., Chatsworth, Calif.) following the manufacturer's instructions.

First strand cDNA from K-562 cells was synthesized in a reaction mixture containing 28 µl of poly d(T)-selected poly(A)$^+$ RNA at a concentration of 0.5 1g/µl and 2.5 µl of 20 pmole/µl first strand primer 6172 (SEQ ID NO: 14) containing an Xho I restriction site. The mixture was heated at 65° C. for 4 minutes and cooled by chilling on ice. First strand cDNA synthesis was initiated by the addition of 16 µl of first strand buffer (5× SUPERSCRIPT™ buffer; GIBCO BRL), 8 µl of 100 mM dithiothreitol and 4 µl of a deoxynucleotide triphosphate solution containing 10 mM each of dATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 µl of 200 U/µl RNase H$^-$ reverse transcriptase (GIBCO BRL). The efficiency of the first strand synthesis was analyzed in a parallel reaction by the addition of 10 µCi of $^{32}$P-αdCTP to a 10 µl aliquot from one of the reaction mixtures to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (Clontech Laboratories). The unincorporated nucleotides in the unlabeled first strand reaction were removed by precipitating the cDNA in the presence of 4 µg of glycogen carrier, 2.5 M ammonium acetate and 2.5 volume ethanol. The unlabeled cDNA was resuspended in 48 µl water for use in second strand synthesis. The length of labeled first strand cDNA was determined by agarose gel electrophoresis.

Second strand synthesis was performed on the first strand cDNA under conditions that promoted first strand priming of second strand synthesis resulting in DNA hairpin formation. Three separate parallel second strand reactions were performed. Each second strand reaction contained 48 µl of the unlabeled first strand cDNA, 16.5 µl of water, 20 µl of 5× polymerase I buffer (100 mM Tris: HCl, pH 7.4, 500 mM KCl, 25 mM MgCl$_2$, 50 mM (NH4)$_2$SO$_4$), 1 µl of 100 mM dithiothreitol, 1 µl of a solution containing 10 mM of each deoxynucleotide triphosphate, 3 µl of 5 mM β-NAD, 1 µl of 3 U/µl E. coli DNA ligase (New England Biolabs Inc.) and 5 µl of 10 U/µl E. coli DNA polymerase I (Amersham Corp.). The reaction was assembled at room temperature and was incubated at room temperature for 5 minutes followed by the addition of 1.5 µl of 2 U/µl RNase H (GIBCO BRL).

A 10 µl aliquot from one of the second strand synthesis reactions was labeled by the addition of 10 µCi $^{32}$P-αdCTP to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories) before analysis by agarose gel electrophoresis. The unlabeled reactions were pooled and extracted with phenol/chloroform and chloroform followed by ethanol precipitation in the presence of 2.5 M ammonium acetate.

The single-stranded DNA of the hairpin structure was cleaved using mung bean nuclease. The reaction mixture contained 100 µl of second strand cDNA, 20 µl of 10× mung bean nuclease buffer (Stratagene Cloning Systems), 16 µl of 100 mM dithiothreitol, 48 µl of water, 10 µl of mung bean nuclease dilution buffer (Stratagene Cloning Systems) and 6 µl of 50 U/µl mung bean nuclease (Promega Corp.). The reaction was incubated at 37° C. for 30 minutes. The reaction was terminated by the addition of 20 µl of 1 M Tris-HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 188 µl of water, was mixed with 50 µl 5×T4 DNA polymerase buffer (250 mM Tris:HCl, pH 8.0, 250 mM KCl, 25 MM MgCl$_2$), 3 µl 0.1 M dithiothreitol, 4 µl of a solution containing 10 mM of each deoxynucleotide triphosphate and 5 µl of 1 U/µl T4 DNA polymerase (Boehringer Mannheim Corp.).

After an incubation of 30 minutes at 15° C., the reaction was terminated by the addition of 10 µl of 0.5 M EDTA followed by serial phenol/chloroform and chloroform extractions as described above. The DNA was chromatographed through a 400 pore size gel filtration column (Clontech Laboratories Inc.) to remove trace levels of protein and to remove short cDNAs less than ~400 bp in length. The DNA was ethanol precipitated in the presence of 10 µg glycogen carrier and 2.5 M ammonium acetate and was resuspended 15 µl of water. Based on the incorporation of $^{32}$P-αdCTP, the yield of cDNA was estimated to be ~8 µg from a starting mRNA template of 40 µg.

Eco RI adapters were ligated onto the 5' ends of the cDNA described above to enable cloning into an expression vector. A 10 µl aliquot of cDNA (~5 µg) and 21 µl of 65 pmole/µl of Eco RI adapter (Pharmacia LKB Biotechnology Inc.) were mixed with 4 µl 10× ligase buffer (Promega Corp.), 3 µl of 10 mM ATP and 3 µl of 15 U/µl T4 DNA ligase (Promega Corp.). The reaction was incubated overnight (~48 hours) at 9° C. The reaction was terminated by the addition of 140 µl of water, 20 µl of 10 × H buffer (Boehringer Mannheim Corp.) and incubation at 65° C. for 40 minutes.

After incubation, the cDNA was extracted with phenol/chloroform and chloroform as described above and precipitated in the presence of 2.5 M ammonium acetate and 1.2 volume of isopropanol. Following centrifugation, the cDNA pellet was washed with 70% ethanol, air dried and resuspended in 89 µl water.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the 6172 primer (SEQ ID NO:14). Restriction enzyme digestion was carried out in a reaction mixture containing 89 μl of cDNA described above, 10 μl of 10× H buffer (Promega Corp.) and 1.5 μl of 40 U/μl Xho I (Boehringer Mannheim Corp.). Digestion was carried out at 37° C. for 1 hour. The reaction was terminated by serial phenol/chloroform and chloroform extractions and chromatography through a 400 pore size gel filtration column (Clontech Laboratories Inc.).

The cDNA was ethanol precipitated, washed with 70% ethanol, air dried and resuspended in 20 μl of 1× gel loading buffer (10 mM Tris-HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel (SEA PLAQUE GTG™ low melt agarose; FMC Corp.). The contaminating adapters and cDNA below 0.5 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) was added to the tube, and the agarose was melted by heating to 65° C. for 15 minutes. Following equilibration of the sample to 45° C., 5 μl of 1 U/μl β-agarase I (New England Biolabs, Inc.) was added, and the mixture was incubated for 90 minutes at 45° C. to digest the agarose. After incubation, 40 μl of 3 M sodium acetate was added to the sample, and the mixture was incubated on ice for 15 minutes. The sample was centrifuged at 14,000×g for 15 minutes at room temperature to remove undigested agarose followed by chromatography through a 400 pore size gel filtration column (Clontech Laboratories). The cDNA was ethanol precipitated, washed in 70% ethanol, air-dried and resuspended in 70 μl water for the kinase reaction to phosphorylate the ligated Eco RI adapters.

To the 70 μl cDNA solution was added 10 μl 10× ligase buffer (Stratagene Cloning Systems), and the mixture was heated to 65° C. for 5 minutes. The mixture was cooled on ice, and 16 μl 10 mM ATP and 4 μl of 10 U/μl T4 polynucleotide kinase (Stratagene Cloning Systems) were added. The reaction mixture was incubated at 37° C. for 1 hour and was terminated by heating to 65° C. for 10 minutes followed by serial extractions with phenol/chloroform and chloroform. The phosphorylated cDNA was ethanol precipitated in the presence of 2.5 M ammonium acetate, washed with 70% ethanol, air dried and resuspended in 10 μl of water. The concentration of the phosphorylated cDNA was estimated to be ~40 fmole/μl.

A λ phage library was then prepared by ligating the Eco RI-Xho I cDNA into Lambda ZAP® II phage arms (Stratagene Cloning Systems) according to the directions of the supplier.

A ZCytor-1 probe was generated by PCR using the #9 subclone in pGEM™-T (Example 2) as a template. The reaction mixture (50 μl total volume) contained 1 pi of template DNA 20 pmoles primer AP2 (Clontech Laboratories), 20 pmoles primer 9672 (SEQ ID NO:13), 5 μl 10× PCR buffer (Boehringer Mannheim), 5 μl 10 mM dNTPs (Perkin-Elmer Corporation), and 2.5 μl Taq polymerase (Boehringer Mannheim). The mixture cycled at 94° C., one minute; 50° C., one minute, 72° C., 1.5 minute for 30 cycles, then incubated at 72° C. for 7 minutes. The resulting 620 bp product was digested with Nar I, which reduced the size to 545 bp and removed any non-coding sequence that was present. The 545 bp fragment was purified by electrophoresis on an agarose gel and designated probe 73457.

The K562 library was plated at 37,000 pfu/plate on 26 NZY plates. Filter lifts were prepared using Hybond N (Amersham Corp., Arlington Heights, Ill.), and 962,000 pfu were screened by hybridization to probe 73457. The filters were washed in 3× SSC, 0.1% SDS for one hour at 65° C. The filters were then prehybridized overnight at 65° C. in 6× SSC, 0.1% SDS, 5× Denhardt's (5' to 3' Inc., Boulder, CO), 100 μg/ml herring sperm DNA (Research Genetics, Huntsville, Ala.). The prehybridization solution was removed and replaced with the same solution containing $1.7 \times 10^6$ cpm/ml of random-labeled 73457 probe, and the filters were hybridized overnight at 65° C. The filters were washed at 65° C. in 0.2× SSC, 0.1% SDS, then exposed to X-ray film overnight. Twenty-six positives were picked from the plates as plugs. DNA was eluted from the plugs and amplified by PCR to confirm the presence of the sequence of interest. 2 μl of eluted phage was amplified using 40 pmoles each of primers 9672 (SEQ ID NO:13) and 9780 (SEQ ID NO:15), 5 μl 10× buffer (Boehringer Mannheim), 5 μl dNTPs (Perkin-Elmer Corporation), and 0.5 μl Taq polymerase (Boehringer Mannheim). The reaction was run for 35 cycles of 94° C., 1 minute; 50° C., 1 minute; 72° C., 1 minute, then incubated at 72° C. for 7 minutes.

Five positives were further purified to single plaques. cDNA inserts were removed using in vivo excision rescue (Uni-ZAP™ XR Cloning Kit, Stratagene Cloning Systems, LaJolla, Calif.). DNA was prepared from the resulting Bluescript™ SK(-) colonies. One clone, designated K7-1-1 P1, was sequenced in its entirety and found to include the fill cDNA shown in SEQ ID NO:2 plus an additional 58 codons in the cytoplasmic domain. The sequence of this clone is shown in SEQ ID NO:4.

EXAMPLE 4

Human Multiple Tissue Northern Blots (Human I, Human II, Human III, and Human Fetal II from Clontech Laboratories, Inc.) were probed to determine the tissue distribution of ZCytor-1 expression. The 160 bp 13—13 PCR fragment (Example 1) was labeled with $^{32}p$ by random priming. The blots were prehybridized in ExpressHyb hybridization solution (Clontech Laboratories, Inc.) at 65° C. for 1—6 hours, then hybridized in ExpressHyb containing $2 \times 10^6$ cpm/ml of 13—13 probe at 65° C. for from 1.5 hour to overnight. After hybridization the blots were washed at 50° C. in 0.1× SSC, 0.1% SDS. A transcript of approximately 3 kb was seen for all tissues probed, with very high levels in spleen, thymus, peripheral blood leukocytes, and lymph nodes. In placenta, a transcript of only 1.0 kb was detected. This smaller transcript was not seen in any other tissue.

EXAMPLE 5

Messenger RNA was prepared from mouse kidney, liver, spleen, and bone marrow tissues by the CsCl method (Chirgwin et al., *Biochemistry* 18:52–94, 1979). Poly(A)$^+$ RNA was prepared from the total RNA by oligo(dt) cellulose chromatography (Aviv and Leder, *Proc. Natl. Acad. Sci. USA* 6:1408–1412, 1972). Double-stranded DNA was prepared from 1 mg of mRNA using a commercially available kit (RT-PCR kit; Stratagene Cloning Systems, La Jolla, Calif.). The DNAs were screened for Zcytor1 sequences by PCR using oligonucleotide primers 9736 (SEQ ID NO:16) and 9740 (SEQ ID NO:17). The PCR conditions were 5 μl 10× buffer (Clontech Laboratories, Inc.), 10 ng single-stranded DNA template, 20 pmol primer, 200 μMol dNTPs, and 1 μl Klentaq DNA polymerase (Clontech Laboratories, Inc.) in a total volume of 50 µl. The reaction mixtures were incubated at 95° C. for one minute, then 30 cycles of 94° C., 30 seconds; 40° C., 30 seconds; 72° C., 45 seconds, followed by a 7 minute incubation at 72° C. Samples were electrophoresed on a 1% agarose gel at 100 V in Tris-borate-EDTA buffer. A band of the expected size (~200 bp) was observed in each sample, with the strongest band observed in the spleen sample. Subsequent sequencing of this band revealed that it was mouse Zcytor1.

Spleen cDNA (prepared essentially as disclosed in Example 3) was cloned into the mammalian expression vector pHZ-1. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. The library was transformed into E. coli DH10b cells. The library, which consisted of 100,000 clones, was divided into 29 pools of 2500 clones each and examined by PCR. PCR was run using 5 µl 10× buffer (Boehringer Mannheim), 0.5 µl Taq DNA polymerase (Boehringer Mannheim), 20 pmol each of primers 9826 (SEQ ID NO:18) and 9827 (SEQ ID NO:19), 200 µmol dNTPs (Perkin Elmer), and 0.5 µl acetylated BSA (10 mg/ml stock, New England Biolabs, Beverly, Mass.) in a total volume of 50 µl. The reaction was run for 3 cycles of 94° C., 30 seconds; 65° C. 30 seconds; 72° C. 1 minute; then 3 cycles of 94° C., 30 seconds, 60° C., 30 seconds; 72° C., 1 minute; then 4 cycles of 94° C., 30 seconds; 55° C., 30 seconds; 72° C., 1 minute; then 30 cycles of 94° C., 30 seconds; 50° C., 30 seconds; 72° C., 1 minute; followed by a 10 minute incubation at 72° C. Two of the pools tested positive.

One of the two positive pools was chosen for plating and screening to isolate mouse Zcytor1 DNA. 1 µl of the pool was used to transform E. coli ElectroMax DH10B™ cells (Life Technologies, Inc., Gaithersburg, Md.) by electroporation. The cells were spread onto LB AMP plates at high density. Colonies were transferred to charged nylon membranes (Amersham Corp., Arlington Heights, Ill.) for probing. Oligonucleotides 9559 (SEQ ID NO:20) and 9560 (SEQ ID NO:21) were labeled using T4 polynucleotide kinase as disclosed by Sambrook et al., Molecular Cloning: A Laboratory Manual, Cold Spring Harbor Laboratory Press, 1989. Unincorporated nucleotides were removed by purifying using a push column (Stratagene Cloning Systems). DNA on the membranes was denatured and neutralized according to standard procedures (Sambrook et al., ibid.), crosslinked to the membranes using a UV crosslinker (Stratalinker®, Stratagene Cloning Systems), then washed with 6× SSC 0.1% SDS to remove bacterial debris. The filters were then prehybridized in 3M trimethylammonium chloride, 0.1 M NaPO$_4$ pH 6.8, 1 mM EDTA, 5× Denhardt's, 100 µg/ml single-stranded DNA for one hour at 53° C. The filters were then hybridized overnight at 53° C. using the above conditions with 2,000,000 cpm/ml probe. Filters were washed 18 hours later in 6× SSC, 0.1% SDS, 0.05% sodium pyrophosphate at temperatures up to 60° C., then placed onto X-ray film. Positives were identified by exposure, and colonies were picked. The identity of the DNA was verified by sequencing and diagnostic PCR reactions.

Two positive clones, designated 7.2 and 11.2, were found to be identical and were determined to encode mouse Zcytor1. The inserts lacked codons corresponding to the N-terminal 5 amino acids of human Zcytor1 (SEQ ID NO:3), but gave the essential sequence information needed for subsequent isolation of full-length clones.

EXAMPLE 6

A full-length mouse Zcytor1 DNA was isolated by PCR from BaF3 cell DNA. Northern blot analysis of a mutagenized BaF3 cell line (24-11 cell line; disclosed in WIPO publication WO 95/21930) showed expression of Zcytor1. Plasmid pools comprising 24-11 DNA cloned into the vector pDX.ES (a mammalian cell expression vector containing a polylinker to facilitate directional cloning of cDNA synthesized with Eco RI-Xho I ends; disclosed in WIPO publication WO 95/21930) were prepared with a Magic miniprep kit (Promega Corp., Madison, Wis.). 51 pools, representing 10,000 colonies each, were prepared.

Pools were screened using PCR reactions and two pairs of primers. Reaction mixtures contained 4 µl pool DNA; 2 µl (40 pmol) of each of primers 9745 (SEQ ID NO:22) and 9757 (SEQ ID NO:23), or primers 9996 (SEQ ID NO:24) and 10002 (SEQ ID NO:25); 5 µl dNTPs (Perkin Elmer); 5 µl 10× Taq polymerase buffer; 0.5 µl Taq DNA polymerase (Boehringer Mannheim); and 31.5 µl dH$_2$O. Reactions were run for 35 cycles of 94° C., 1 minute; 55° C., 1 minute; 72° C., 1 minute, followed by a 7 minute incubation at 72° C. Two pools, $T_a34$ and $T_a43$, each gave a 448 bp product with primers 9745 and 9757, and a 425, bp product with primers 9996 and 10002.

Smaller pools from $T_a34$ and $T_a43$ were then screened. Reactions were run as above, but using 1 µl of pool DNA and 34.5 µl of H$_2$O and primers 9745 (SEQ ID NO:22) and 9757 (SEQ ID NO:23). One of the smaller pools from $T_a34$ gave a 448 bp band. Screening with primers 9996 (SEQ ID NO:24) and 10002 (SEQ ID NO:25) yielded a 425 bp band from one of the smaller pools from pool $T_a43$. Additional screening confirmed the presence of Zcytor1 DNA in these pools.

DNA from the two positive small pools was transformed by electroporation into competent E. coli cells (FJP101 cells; Life Technologies, Inc.). 40 µl of competent cells and 1 µl of DNA were combined on ice. The cells were electroporated at 1.8 kV, 200Ω, 25 µF. The mixture was added to 1 ml of room temperature SOC (2% Bacto™-tryptone (Difco, Detroit, Mich.), 0.5% Bacto™ yeast extract (Difco), 10 mM NaCl, 2.5 mM KCl, 10 mM MgCl$_2$, 10 mM MgSO$_4$, 20 mM glucose). Ten µl of $10^{-1}$, $10^{-2}$, and $10^{-3}$ dilutions of the cell suspension were plated on LB+ampicillin plates. Colonies were grown overnight at 37° C.

To screen for the presence of Zcytor1 DNA, colonies were transferred to filters, denatured in 0.5 N NaOH containing 1.5 M NaCl, and neutralized in 1 M Tris pH 7.5, 1.5 M NaCl. DNA was cross-linked to the filters using a UV crosslinker. The filters were washed at 65° C. in 2× SSC, 0.1% SDS, then prehybridized for 3 hours at 65° C. in 6× SSC, 0.1% SDS, 5× Denhardt's, 0.1 mg/ml herring sperm DNA. The filters were probed with the 448 bp PCR product disclosed above, which was labeled with $^{32}$P αdATP using a commercially available kit (Multiprime™ DNA labeling system; Amersham Corp.). The probe was purified over a push column (obtained from Stratagene Cloning Systems). The filters were hybridized to the probe (1.7×10$^6$ cpm/ml in prehybridization solution) at 65° C. for 3 days. The filters were then washed in 0.2× SSC, 0.1% SDS four times at room temperature (brief rinses), 20 minutes at room temperature, then 2×20 minutes at 65° C. Filters were exposed to X-ray film for 3 hours at −80° C. One positive colony from each set of electroporations was picked. Liquid and solid cultures were prepared using LB+ampicillin.

DNA was prepared from the cultures by the miniprep procedure and analyzed by restriction endonuclease digestion and PCR using vector and internal primers. Ten colonies were picked from each set and screened by PCR using internal primers 9745 (SEQ ID NO:22) and 9757 (SEQ ID NO:23). Reaction mixtures containing 2 μl of each primer; 5 μl dNTPs (Perkin-Elmer Corporation); 5 μl 10× Taq polymerase buffer (Boehringer Mannheim); 0.5 μl Taq DNA polymerase (Boehringer Mannheim); and 35.5 μl dH$_2$O were placed in tubes and individual colonies were added. Reactions were run for 35 cycles of 94° C., 1 minute; 55° C., 1 minute; 72° C., 1 minute, followed by a 7 minute incubation at 72° C. One correct colony from each set was streaked on LB+ampicillin plates.

The two positive clones were sequenced, and both were found to encode full-length Zcytor1. One clone, T1323D, was selected for expression vector construction. The nucleotide sequence and deduced amino acid sequence of the T1323D insert are shown in SEQ ID NOS:6 and 7, respectively. Alignment of the mouse and longer human (SEQ ID NO:5) sequences shows an amino acid sequence identity of approximately 62%.

EXAMPLE 7

An expression vector encoding a polyhistidine-tagged soluble mouse Zcytor1 was constructed. The primary translation product comprised the secretory peptide and extracellular domain of Zcytor1 followed by a spacer peptide (Gly-Gly-Ser-Gly; SEQ ID NO:26) and six histidine residues.

The full-length mouse Zcytor1 clone, T1323D, was digested with EcoRI and ApaI, and a 1500 bp fragment was recovered.

A second DNA fragment was generated by PCR using T1323 as a template. 100 ng plasmid DNA was combined with 20 pmole of each of primers 10302 (SEQ ID NO:27) and 10305 (SEQ ID NO:28), 5 μl 10× buffer (Clontech Laboratories, Inc.), 5 μl 10 mM dNTPs (Perkin-Elmer Corporation), and 1 μl Klentaq polymerase (Clontech Laboratories, Inc.) in a total volume of 50 μl. The reaction was run for 15 cycles of 94° C., 1 minute; 45° C., 1 minute; 72° C., 1 minute, followed by a 7 minute incubation at 72° C. The resulting 440 bp product was digested with ApaI and XhoI and electrophoresed on a 1% agarose gel. A 65 bp fragment was eluted from the gel and recovered.

The 1500 bp and 65 bp fragments were then ligated to the plasmid pHZ200 HIS TAG that had been cleaved with EcoRI and XhoI. This plasmid is a mammalian cell expression vector comprising the mouse metallothionein-1 promoter; the bacteriophage T7 promoter flanked by multiple cloning banks containing unique restriction sites for insertion of coding sequences; the human growth hormone terminator; the bacteriophage T7 terminator; an *E. coli* origin of replication; a bacterial beta lactamase gene; a mammalian selectable marker expression unit comprising the SV40 promoter and origin, a DHFR gene, and the SV40 transcription terminator; and a sequence encoding a C-terminal polyhistidine tag downstream of the MT-1 promoter. *E. coli* DH10B cells were transformed with the resulting construct, and plasmid DNA was prepared by the alkaline lysis method (Sambrook et al., *Molecular Cloning: A Laboratory Manual*, 2nd ed., Cold Spring Harbor Laboratory Press, 1989) from four colonies. A portion of the plasmid DNA was sequenced to confirm its identity, then transfected into BHK 570 cells by liposome-mediated transfection (Lipofectamine™ reagent, Life Technologies, Inc.). Transfected colonies were selected in 1 μM methotrexate. Conditioned serum-free medium was collected, and the soluble receptor polypeptide was isolated on a nickel-agarose resin (Qiagen, Inc., Chatsworth, Calif.). The isolated protein was electrophoresed on a 7.5% SDS-polyacrylamide gel (Integrated Separation Systems, Natick, Mass.). A band of approximately 75 kD was observed.

EXAMPLE 8

Expression vector encoding human and mouse Zcytor1-IgG fusion proteins was constructed. The fusions comprised the extracellular domain of each Zcytor1 fused at its C-terminus (residue 514 of human Zcytor1, SEQ ID NO:3; residue 508 of mouse Zcytor1, SEQ ID NO:7) to the hinge region of the Fc portion of an IgG$_{g1}$ (Ellison et al., *Nuc. Acids Res.* 10:4071–4079, 1982). The hinge region was modified to replace a cysteine residue with serine to avoid unpaired cysteines upon dimerization of the fusion protein.

Human Zcytor1 DNA fragments were prepared from a K7-1-1 PI (Example 3) template. A 0.177 kb ApaLI-BglII fragment was prepared by PCR using 1 μl of oligonucleotide primer ZG10381 (SEQ ID NO:29) and 4.9 μl of ZG10390 (SEQ ID NO:30). The primers were combined with 1 μl of template DNA, 10 μl of 2.5 mM dNTPs (Perkin-Elmer Corp.), 10 μl of 10× buffer (Klentaq PCR buffer, Clontech Laboratories, Inc.), 2 μl of Klentaq DNA polymerase (Clontech Laboratories, Inc.), and 71.1 μl H$_2$O. The reaction was run for 35 cycles of 94° C., 1 minute; 55° C., 1 minute; and 72° C., 2 minutes; followed by a 7-minute incubation at 720C. The reaction products were extracted with phenol/CHCl$_3$, precipitated with ethanol, and digested with BglII. The DNA was electrophoresed on a agarose gel, and a 177 bp fragment was electrophoretically eluted from a gel slice, purified by phenol/CHCl$_3$ extraction, and precipitated with ethanol. A second fragment (1.512 kb) was isolated from the cDNA by digestion with EcoRI and ApaLI.

A human IgG$_{g1}$ clone was isolated from a human fetal liver cDNA library (Clontech Laboratories, Inc.) by PCR using oligonucleotide primers ZG10314 (SEQ ID NO:31) and ZG10315 (SEQ ID NO:32). The former primer introduced a BglII site into the hinge region (changing the third residue of the hinge region from Lys to Arg) and replaced the fifth residue of the hinge region (Cys) with Ser. PCR was carried out essentially as described above for the Zcytor1 reactions. The DNA was digested with EcoRI and XbaI, and a 0.7 kb fragment was recovered by agarose gel electrophoresis, electroelution, phenol/CHCl$_3$ extraction, and ethanol precipitation. The IgG-encoding fragment and an XbaI-EcoRI linker were ligated into Zem229R (ATCC Accession No. 69447) that had been digested with EcoRI and treated with calf intestinal phosphatase. The resulting plasmid was designated Zem229R IgGγ1#488.

To construct an expression vector for the human Zcytor1-IgG fusion, Zem229R IgGγ1#488 was digested with EcoRI and BglII. The linearized vector was ligated to the two human Zcytor1 fragments. The resulting construct was designated hZYCTOR-1/IgG #641.

Mouse Zcytor1 DNA fragments were prepared from a T1323D (Example 6) template. A 0.379 kb KpnI-BglII fragment was prepared by PCR essentially as described above using oligonucleotide primers 10382 (SEQ ID NO:33) and 10388 (SEQ ID NO:34). The PCR product was digested with ApaI and gel purified to yield a 46 bp ApaI-BglII fragment. A 1.5 kb fragment was prepared from mZCYTOR-1 T1323 by digestion with EcoRI and ApaI.

The two mouse DNA fragments were ligated to Zem229R IgGγ1#488 that had been digested with EcoRI and BglII. The resulting construct was designated mZYCTOR-1/IgG #632.

The mouse and human Zcytor1/IgG fusion constructs were each transfected into BHK-570 cells by liposome-mediated transfection. Transfectants were cultured in medium containing 1 μM methotrexate for 10 days.

Fusion proteins were purified from cell-conditioned media using protein A-Sepharose. Purified protein was used to immunize animals (mice or rabbits) to generate anti-receptor antibodies. Fusion proteins were also used coupled to a BIAcore™ biosensor for use in assays.

EXAMPLE 9

Human and mouse Zcytor1 proteins were expressed in *E. coli* as in-frame fusions behind the *E. coli* maltose binding protein (MBP). The resulting MBP-Zcytor1 fusion proteins were purified by affinity chromatography on an amylose-Sepharose matrix. The purified proteins were subsequently used to elicit a polyclonal antibody response in rats and rabbits.

The ligand-binding domain coding sequence of the human Zcytor1 cDNA was amplified from a plasmid containing the full-length sequence (K7-1-1 P1). PCR amplification was run under conventional reaction conditions using Taq polymerase and buffer (both obtained from Boehringer Mannheim) and 20 pmol of each of primers 10123 (SEQ ID NO:35) and 10116 (SEQ ID NO:36). The reaction was run for 30 cycles of 94° C., 30 seconds; 50° C., 30 seconds; and 720C, 1 minute; followed by incubation at 72° C. for 6 minutes. The reaction products were purified by extraction with phenol:chloroform:isoamylalcohol 24:24: 1, precipitated with ethanol, and digested with BamHI and EcoRI.

A double-stranded linker was prepared using oligonucleotides 10124 (SEQ ID NO:37) and 10122 (SEQ ID NO:38). The oligonucleotides were annealed and kinased. The resulting linker provided the 5' end of the Zcytor1 coding sequence, as well as XmnI and BamHI cleavage sites.

To construct an expression vector, the plasmid pMAL™-c2 (New England Biolabs) was digested with XmnI and EcoRI and treated with calf intestinal phosphatase. The linearized vector and the purified PCR product were purified by gel electrophoresis. The vector, insert, and linker were ligated, and the resulting construct was transformed into E. coli MC1061 (Clontech Laboratories, Inc.). Individual colonies were chosen for further study. Colonies harboring the desired fusion construct were identified by restriction analysis of plasmid DNA. The correct construct was verified by sequencing and designated pSDH38.

DNA encoding mouse Zcytor1 ligand binding domain was amplified by PCR using a plasmid containing the full-length sequence as template and oligonucleotide primers 10182 (SEQ ID NO:39) and 10200 (SEQ ID NO:40). The reaction was run as described above for the human sequence. The purified PCR product was digested with BamHI and XhoI.

A double-stranded linker was prepared using oligonucleotides 10184 (SEQ ID NO:41) and 10183 (SEQ ID NO:42). The oligonucleotides were annealed and kinased. The resulting linker provided the 5' end of the Zcytor1 coding sequence, as well as XmnI and BamHI cleavage sites.

To construct an expression vector, the plasmid pMAL™-c2 was digested with XmnI and SalI and treated with calf intestinal phosphatase. The linearized vector and the purified PCR product were purified by gel electrophoresis. The vector, insert, and linker were ligated, and the resulting construct was transformed into E. coli MC1061 (Clontech Laboratories, Inc.). Individual colonies were chosen for further study. Colonies harboring the desired fusion construct were identified by restriction analysis of plasmid DNA. The correct construct was verified by sequencing and designated pCZR154.

E. coli MC1061 strains carrying the MBP::Zcytor1 fusion constructs were inoculated from fresh LB+Amp plates into 5 ml Terrific broth (containing, per liter, 12 g Bacto™ tryptone (Difco Laboratories, Detroit, Mich.), 24 g Bacto™ yeast extract (Difco Laboratories), 9.2 g potassium phosphate dibasic, 2.2 g potassium phosphate monobasic, and 4 ml glycerol) containing 100 µg/ml ampicillin to an approximate cell density of $10^7$ cells/ml ($OD_{600}$=0.1). After two hours of growth at 37° C., expression of the fusion proteins was induced by addition of IPTG to a final concentration of 1 mM. Cultures were incubated for an additional three hours.

Protein extracts were prepared from IPTG-induced and uninduced control cultures for subsequent analysis by SDS-PAGE and Western blotting. One ml of culture was harvested by centrifugation, and the cell pellet was disrupted in 400 µl of Thorner buffer (8 M urea, 5% SDS, 10% glycerol, 100 mM Tris pH 7.0, 2 mM EDTA) containing 0.01% bromphenol blue and 2% β-mercaptoethanol by vigorous vortexing with 100 µl glass beads and heating to 65° C. The samples were then boiled and clarified by centrifugation. Two-el aliquots of the clarified samples were analyzed by electrophoresis on 8–16% SDS-polyacrylamide glycine gels (Novex, San Diego, Calif.). Staining with Coomassie blue revealed the presence of a 66 kD band in the induced samples that was not present in uninduced cells. Western blotting with an anti-MBP serum (New England Biolabs) demonstrated that the induced bands were the desired human and mouse MBP::Zcytor1 fusion proteins.

Large (1 liter) cultures of IPTG-induced E. coli cells containing the mouse (pCZR154) or human (pSDH38) Zcytor1 expression vectors were prepared. Cells were grown in Terrific broth containing 100 µg/ml ampicillin. Expression and purification protocols supplied with the MBP vector were followed. SDS-PAGE analysis of the purified proteins indicated that the fusions represented ≧70% of total protein. Sufficient quantities of each fusion protein were prepared to allow immunization of rats and rabbits and to affinity purify the resulting antibodies.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An antibody that specifically binds to a polypeptide comprising a segment selected from the group consisting of:
   (a) residues 33 to 235 of SEQ ID NO:3; and
   (b) residues 25–229 of SEQ ID NO:7.

2. The antibody of claim 1, wherein said polypeptide comprises residues 33 to 514 of SEQ ID NO:3 or residues 25 to 508 of SEQ ID NO:7.

3. The antibody of claim 1, wherein said antibody is a monoclonal antibody.

4. The antibody of claim 1, wherein said antibody is selected from the group consisting of F(ab')$_2$ fragments and Fab fragments.

5. A composition comprising the antibody of claim 1 and an adjuvant.

* * * * *